US007026464B2

(12) United States Patent
Dicosimo et al.

(10) Patent No.: US 7,026,464 B2
(45) Date of Patent: Apr. 11, 2006

(54) NATURAL PROMOTERS FOR GENE EXPRESSION IN C1 METABOLIZING BACTERIA

(75) Inventors: Deana J. Dicosimo, Rockland, DE (US); Hao Ni, New Castle, DE (US); Stephen K. Picataggio, Wilmington, DE (US); John E. Seip, Alloway, NJ (US); Rick W. Ye, Hockessin, DE (US); Tao Wang, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 122 days.

(21) Appl. No.: 10/689,200

(22) Filed: Oct. 20, 2003

(65) Prior Publication Data

US 2004/0126848 A1 Jul. 1, 2004

Related U.S. Application Data

(60) Provisional application No. 60/419,872, filed on Oct. 21, 2002.

(51) Int. Cl.
C07H 21/04 (2006.01)
(52) U.S. Cl. .................................. 536/23.1
(58) Field of Classification Search ............... 536/23.1, 536/24.1
See application file for complete search history.

(56) References Cited

U.S. PATENT DOCUMENTS 4,348,476 A 9/1982 Hou
6,331,428 B1 12/2001 Kato et al.

FOREIGN PATENT DOCUMENTS

| WO | WO 9633821 A1 | 10/1996 |
| WO | WO 02/18617 A2 | 3/2002 |
| WO | WO 02/20733 A2 | 3/2002 |
| WO | WO 02/20797 A2 | 3/2002 |
| WO | WO 02/20728 A2 | 3/2003 |

OTHER PUBLICATIONS

Morris et al., Cloning of amethanol-inducible moxF promoter and its analysis in moxB mutants of Methylobacterium extorquens AM1rif. Journal of Bacteriology, Jul. 1992, vol. 174, N. 13, pp. 4444-4449, abstract.
Sharpe, Production of single cell protein Sharpe, D.H. BioProtein Manufacture, 1989. Hellis Horwood series in applied science and industrial technology, New York: Halstead Press.
Villadsen, J., Recent Trends Chem. React. Eng., Proc. Int. Chem, React. Eng. Conf., 2nd 1987, vol. 2, pp. 320-333, Editors(s): Kulkami, B.D.; Mashelkar, R. A.; Sharma, M. M. Publisher: Wiley East, New Delhi.

Naguib, M, Proc. OAPEC Symp. Petroprotein, Pap., 1980, Meeting Date 1979, pp. 253-277, Publisher: Organ. ArabPet. Exporting Countries,Kuwait, Kuwait.
Tsien et al., Biodegradation of chlorinated pollutants, Pap. Int. IGT Symp. Gas, Oil, Coal, Enviorn. Biotechnol., 2nd, 1990, pp. 83-104, Editor(s): Akin, Cavit; Smith, Jared. Publisher: Inst. Gas Technol., Chicago, IL.
Merkley et al., Biorem. Recalcitrant Org., Pap. Int. In Situ On-site Bioreclam. Symp., 3rd, 1995, pp 165-174. Editor(s): Hinchee, Robert E. Anderson, Daniel B.; Hoeppel, Ronald E. Publisher: Battelle Press, Columbus, OH.
Meyer et al., Development of techniques for the bioremediation of soil, air and groundwater polluted with chlorinated hydrocarbons: the demonstration project at the model site in Eppelheim, Microb. Releases:2(1): 11-22, 1993.
Ivanova et al.,Production of Organic Exomethabolites by Diverse Cultures of Obligate Methanotrophes, Mikrobiologiya 57(4): 600-5, 1988.
Kilbane, John J., II Gas, Oil, Coa, Environ. Biotechnol. 3, Pap. IGT's Int. Symp., 3rd, 1991, Meeting Date 1990, pp. 207-206, Editor(s): Akin, Cavit: Smith, Jared. Publisher: IGT, Chicago, IL.
Urakami et al., Occurrence of Isoprenoid Compounds in Gram-Negative Methanol-, Methane3-, and Methylamine-Utilizing Bacteria, J. Gen. Appl. Microbiol. 32(4): 317-41, 1986.
Frias, J. E., et al., Nitrate assimilation gene cluster from the heterocyst-forming cyanobacterium Anabeana sp.Strain PCC 7120, Journal of Bacteriology, Jan. 1997, pp. 477-486, vol. 179, No. 2.
Meletzus, D., et al., Characterization of the ginK-amtB operon of Azotobacter vinelandii, J. Bactreriol. 180(12): 3260-3264, 1998.
Arabidopsis thaliana, Mar. 31, 2001, Accession H96575.
Theologis, A., et al., Sequence and analysis of chromosome 1 of the plant Arabidopsis thaliana, Nature 408, 6814, pp. 816-820, 2000.
Bardwell J. C. A., Craig E.A.; Eukaryotic Mr 83,000 heat shock protein has a homologue in Escherichia coli, Proc. Natl. Acad. Sci. U. S. A., 84: pp. 5177-5181, 1987.
Waechter-Brulla, D., et al., Methanol oxidation genes in the marine methanotroph Methylomonas sp. Strain A4, J. Bacteriol. 175(12): pp. 3767-3775, 1993.
Aminomonas aminovorus, Jul. 29, 2002, Gene Bank Acc. No. AAG29505.
Morris et al., Cloning of amethanol-inducible moxF promoter and its analysis in moxB mutants of Methylobacterium extorquens AM1rif. Journal of Bacteriology, Jul. 1992, vol. 174, N. 13, pp. 4444-4449, abstract.

*Primary Examiner*—Nancy Vogel

(57) ABSTRACT

Genes have been identified in the *Methylomonas* genome that are responsive to various metabolic and growth conditions. The identified responsiveness of these genes allows for the use of their promoters in regulated gene expression in C1 metabolizing bacteria. In particular, the hps promoter, which in its native state drives the expression of 3-hexulose-6-phosphate synthase (HPS), was found to be useful for directing expression of heterolgous coding regions (e.g., crtZ) in the obligate methanotroph *Methylomonas* sp. 16a.

3 Claims, 3 Drawing Sheets

(A)

(B)

SEQUENCE LISTING

<160> NUMBER OF SEQ ID NOS: 26

<210> SEQ ID NO 1
<211> LENGTH: 1392
<212> TYPE: DNA
<213> ORGANISM: Methylomonas sp. 16a

<400> SEQUENCE: 1

| | | | | | | |
|---|---|---|---|---|---|---|
| atgaaaacca | tcattagatc | gagctcgaag | aaattgttat | tgacgttatc | ggcttcgcta | 60 |
| gccgtttggg | gtttgacgat | tgcgcccgat | gtcggggcag | ttggcaagct | ggaaaaggaa | 120 |
| gatttgaaat | tcggcttcat | caagctcacc | gacatggcgc | cgctggcggt | ggccgccgaa | 180 |
| aaaggcttct | tcgaggacga | gggcctgttc | gtgcaactgg | aagcgcaggc | caactggaag | 240 |
| gtggtgatgg | atagggtcgt | gaatggcgaa | ctggacggct | cgcacatgct | ggcgccggcg | 300 |
| ccgttagcgg | ccagcgttgg | cttcggcacc | aaggccgata | tcgaggtgcc | gttcagcatg | 360 |
| ggcttcaacg | gcaacgcgat | tacggtgtcc | aatgaaatct | ggcatcagat | gaagccgaac | 420 |
| ataccgctgg | aaggcggtaa | accggtgcat | ccgatcaagg | cagattatct | aaaaccggtc | 480 |
| gtcgaaaaat | acaaagccga | aggcaagccg | ttcaatatgg | cgatgacctt | cccggccgga | 540 |
| tctcacaaca | tcaaactgcg | ttactggctg | gcggctggcg | gtatcaatcc | tggctactat | 600 |
| tcgccgccgc | aggacatttc | cggccaaatc | ggcgcagacg | ccttgttgtc | ggtgaccccg | 660 |
| ccgccgcaaa | tgccgtccac | gctggaagcc | ggcaccattt | tcggttattg | cgtcggcgag | 720 |
| ccgtggaacc | agcaggccgt | gttcaagggc | ataggcgtgc | cggtgatcac | cgatgaagaa | 780 |
| ctctggaagg | acacgccgga | aaaagtcttc | ggcgtgacca | acaatgggc | ggagaaatac | 840 |
| cccaacacct | atctggcggt | gaccaaggcg | ctgattcggg | ccgcgatctg | gctggacgcc | 900 |
| gacaataaca | agaaccgcaa | ggaagccatc | gaaatgctgg | cgcaaaaaca | atacgtcggt | 960 |
| gctgacgtgg | aagtgctggc | ggctagcatg | aacggcactt | tcgaatacga | aaaagacgat | 1020 |
| aaacgcgcgc | taccggactt | caacaccttc | tttcgccacg | gcgccagcta | tccgtcctac | 1080 |
| agcagtgcag | tctggtatct | gacccagctg | aggcgctggg | gcatgatcaa | tgaattcaaa | 1140 |
| ccggacaact | ggtatctgga | taccgccaag | aacgtctacc | gcccggacat | ctatctcgcc | 1200 |
| gcggccaagg | aactggtcgc | agaaggcaag | gccaaggccg | aagacttccc | tgccgatacc | 1260 |
| tcgatcaagc | cgtcgcagaa | tttcttcatc | gacaaagtgc | cgttcgatgc | caacaagccc | 1320 |
| aacgattacc | tcgccaagtt | tgcgataggt | ctgaaaggca | agcaaaccgt | agccggcggc | 1380 |
| aaggtcgtgg | at | | | | | 1392 |

```
<210> SEQ ID NO 2
<211> LENGTH: 464
<212> TYPE: PRT
<213> ORGANISM: Methylomonas sp. 16a

<400> SEQUENCE: 2

Met Lys Thr Ile Ile Arg Ser Ser Lys Lys Leu Leu Thr Leu
1               5                   10                  15

Ser Ala Ser Leu Ala Val Trp Gly Leu Thr Ile Ala Pro Asp Val Gly
            20                  25                  30

Ala Val Gly Lys Leu Glu Lys Glu Asp Leu Lys Phe Gly Phe Ile Lys
        35                  40                  45

Leu Thr Asp Met Ala Pro Leu Ala Val Ala Ala Glu Lys Gly Phe Phe
50                  55                  60

Glu Asp Glu Gly Leu Phe Val Gln Leu Glu Ala Gln Ala Asn Trp Lys
65                  70                  75                  80

Val Val Met Asp Arg Val Val Asn Gly Glu Leu Asp Gly Ser His Met
                85                  90                  95

Leu Ala Pro Ala Pro Leu Ala Ala Ser Val Gly Phe Gly Thr Lys Ala
            100                 105                 110

Asp Ile Glu Val Pro Phe Ser Met Gly Phe Asn Gly Asn Ala Ile Thr
        115                 120                 125

Val Ser Asn Glu Ile Trp His Gln Met Lys Pro Asn Ile Pro Leu Glu
130                 135                 140

Gly Gly Lys Pro Val His Pro Ile Lys Ala Asp Tyr Leu Lys Pro Val
145                 150                 155                 160

Val Glu Lys Tyr Lys Ala Glu Gly Lys Pro Phe Asn Met Ala Met Thr
                165                 170                 175

Phe Pro Ala Gly Ser His Asn Ile Lys Leu Arg Tyr Trp Leu Ala Ala
            180                 185                 190

Gly Gly Ile Asn Pro Gly Tyr Tyr Ser Pro Pro Gln Asp Ile Ser Gly
        195                 200                 205

Gln Ile Gly Ala Asp Ala Leu Leu Ser Val Thr Pro Pro Gln Met
210                 215                 220

Pro Ser Thr Leu Glu Ala Gly Thr Ile Phe Gly Tyr Cys Val Gly Glu
225                 230                 235                 240

Pro Trp Asn Gln Gln Ala Val Phe Lys Gly Ile Gly Val Pro Val Ile
                245                 250                 255

Thr Asp Glu Glu Leu Trp Lys Asp Thr Pro Glu Lys Val Phe Gly Val
            260                 265                 270

Thr Lys Gln Trp Ala Glu Lys Tyr Pro Asn Thr Tyr Leu Ala Val Thr
        275                 280                 285

Lys Ala Leu Ile Arg Ala Ala Ile Trp Leu Asp Ala Asp Asn Asn Lys
290                 295                 300

Asn Arg Lys Glu Ala Ile Glu Met Leu Ala Gln Lys Gln Tyr Val Gly
305                 310                 315                 320

Ala Asp Val Glu Val Leu Ala Ala Ser Met Asn Gly Thr Phe Glu Tyr
                325                 330                 335

Glu Lys Asp Asp Lys Arg Ala Leu Pro Asp Phe Asn Thr Phe Arg
            340                 345                 350

His Gly Ala Ser Tyr Pro Ser Tyr Ser Ser Ala Val Trp Tyr Leu Thr
        355                 360                 365

Gln Leu Arg Arg Trp Gly Met Ile Asn Glu Phe Lys Pro Asp Asn Trp
370                 375                 380
```

Tyr Leu Asp Thr Ala Lys Asn Val Tyr Arg Pro Asp Ile Tyr Leu Ala
385                 390                 395                 400

Ala Ala Lys Glu Leu Val Ala Glu Gly Lys Ala Lys Ala Glu Asp Phe
            405                 410                 415

Pro Ala Asp Thr Ser Ile Lys Pro Ser Gln Asn Phe Phe Ile Asp Lys
                420                 425                 430

Val Pro Phe Asp Ala Asn Lys Pro Asn Asp Tyr Leu Ala Lys Phe Ala
            435                 440                 445

Ile Gly Leu Lys Gly Lys Gln Thr Val Ala Gly Lys Val Val Asp
    450                 455                 460

<210> SEQ ID NO 3
<211> LENGTH: 551
<212> TYPE: DNA
<213> ORGANISM: Methylomonas sp. 16a
<220> FEATURE:
<221> NAME/KEY: misc_feature
<222> LOCATION: (409)..(411)
<223> OTHER INFORMATION: ATG start site of nrtA gene

<400> SEQUENCE: 3

```
acacgctcaa gcgaaccacg cccaatttac tcatatgcct atgatttaaa tattgaaata      60
aaattcatta gttccaaggt acgagcttgg cattgcgatt gcttgggata ttgtcagaaa     120
taacttccct gtgtatctcc tttcccagag aaggcggtcg taatccccct ctccccgcgg     180
gtgcggaggg agaaggcact gttttgactc atccaacaga ggatgaggac gcacaatgcg     240
gaagttattt ttgactgaat tattagtatc aatcagcact ccatcgtagg agtctgaatt     300
ttcgctcacg ggtgagcaaa tcggacgaag gcgtctgtcg tgcattgctt ttggcaatga     360
cacgcggacg ccttttttat tttccgccgt ttttgtttgg aactagtcat gaaaaccatc     420
attagatcga gctcgaagaa attgttattg acgttatcgg cttcgctagc cgtttggggt     480
ttgacgattg cgcccgatgt cggggcagtt ggcaagctgg aaaaggaaga tttgaaattc     540
ggcttcatca a                                                         551
```

<210> SEQ ID NO 4
<211> LENGTH: 336
<212> TYPE: DNA
<213> ORGANISM: Methylomonas sp. 16a

<400> SEQUENCE: 4

```
atgaaactca taacagcagt tgtaaagcca ttcaagctcg acgacgtccg tgaggcgttg      60
tccgagattg gcgtatccgg ggtgacggtg accgaagtca agggctttgg ccgtcagaaa     120
gggcataccg aactctatcg aggtgccgag tacgtagtca atttcttgcc caaggccaaa     180
atcgaagtgg cggtggggga tgccttggtc gagcaggcgg tagagtccat cgtcaaggtg     240
gccaataccg gcaaaatcgg cgacggcaag atttcgtca ccaatttaga gcaggttgtc     300
cggatcagaa ccggcgaatc cggcgaagac gcgctt                              336
```

<210> SEQ ID NO 5
<211> LENGTH: 112
<212> TYPE: PRT
<213> ORGANISM: Methylomonas sp. 16a

<400> SEQUENCE: 5

Met Lys Leu Ile Thr Ala Val Val Lys Pro Phe Lys Leu Asp Asp Val
1               5                   10                  15

```
Arg Glu Ala Leu Ser Glu Ile Gly Val Ser Gly Val Thr Val Thr Glu
            20                  25                  30

Val Lys Gly Phe Gly Arg Gln Lys Gly His Thr Glu Leu Tyr Arg Gly
        35                  40                  45

Ala Glu Tyr Val Val Asp Phe Leu Pro Lys Ala Lys Ile Glu Val Ala
    50                  55                  60

Val Gly Asp Ala Leu Val Glu Gln Ala Val Glu Ser Ile Val Lys Val
65                  70                  75                  80

Ala Asn Thr Gly Lys Ile Gly Asp Gly Lys Ile Phe Val Thr Asn Leu
                85                  90                  95

Glu Gln Val Val Arg Ile Arg Thr Gly Glu Ser Gly Glu Asp Ala Leu
            100                 105                 110

<210> SEQ ID NO 6
<211> LENGTH: 551
<212> TYPE: DNA
<213> ORGANISM: Methylomonas sp. 16a
<220> FEATURE:
<221> NAME/KEY: misc_feature
<222> LOCATION: (445)..(447)
<223> OTHER INFORMATION: ATG start site of nitrogen regulating
              PII-protein (glnB) gene

<400> SEQUENCE: 6
gctttcgttc aaaataattc tctccgtcag ggaaaagaga ggctaggggg gttatccgaa      60
gcatttctgc aggcctattt tccatatggc tttcgtaaaa gatcaaatgt agcttggatc     120
cgcgtcgcat aagtcaacga aatcagaatg ttgagatgca gtctaacctg ttttttgtga     180
tgcccgcttc aaagggtaaa gctgggcgga atttcgggtg tattgatgac acgttcctta     240
ttaatcccgt gcctgcgcaa aaagggcggt accaaaatga agcgccgtgc gccaagttgg     300
tgcttcaaaa tggggattgc aaacgggttt cataaaaagt cttttaataa caattgatta     360
tgtgttggca tgtaacgtgc ttattcgctc gtgaagttaa tgacaagtcg ttttggggga     420
attaaccatg agaggtatca atttatgaaa ctcataacag cagttgtaaa gccattcaag     480
ctcgacgacg tccgtgaggc gttgtccgag attggcgtat ccggggtgac ggtgaccgaa     540
gtcaagggct t                                                         551

<210> SEQ ID NO 7
<211> LENGTH: 693
<212> TYPE: DNA
<213> ORGANISM: Methylomonas sp. 16a

<400> SEQUENCE: 7
atgattttca agcaactttt cgaaaccgaa acatcgacct atagctattt gctgggctgt      60
gaacgcactc accgcgcgat ttaatcgat ccggtcgcct cggaactgga tgactatatc      120
gatctgttga atagcctgac tctcaaattg atttataccc tggaaacgca cgttcatgcg     180
gaccacatca ccggctccgg actgctacgg caaaagcttg gcagcaaaag tgtcgtgcat     240
cgagatgcgg gcgccatgtg cgcggaccte ctggtcaccg atggcgtacc actgcaagtc     300
ggcgacctgg aattagaagt ccgacatacg cccggccaca ccaatggctg cgtcagttac     360
gtgatggccg accgggtctt caccggtgat gcactattga tcggcggcag cggccgtacc     420
gattttcaac aaggcgacgc tggccaactt tacgacagca tcaccggcaa gctgttcaca     480
ttgccacccg acaccctggt ttatcctgga cacgattaca acggcaacac cgtttccacg     540
atcaaacaag agatggccaa aaacacgcgc ttgggcggcg gcaaatcacg cgaggaattc     600
```

```
atcgccatcc tgcaagattt gaaactggct tatcccaagt tcatcgataa ggccttaccg      660
gccaatcaat cctgcggctt gatcgcacag ggt                                  693
```

<210> SEQ ID NO 8
<211> LENGTH: 231
<212> TYPE: PRT
<213> ORGANISM: Methylomonas sp. 16a

<400> SEQUENCE: 8

```
Met Ile Phe Lys Gln Leu Phe Glu Thr Glu Thr Ser Thr Tyr Ser Tyr
1               5                   10                  15

Leu Leu Gly Cys Glu Arg Thr His Arg Ala Ile Leu Ile Asp Pro Val
            20                  25                  30

Ala Ser Glu Leu Asp Asp Tyr Ile Asp Leu Leu Asn Ser Leu Thr Leu
        35                  40                  45

Lys Leu Ile Tyr Thr Leu Glu Thr His Val His Ala Asp His Ile Thr
    50                  55                  60

Gly Ser Gly Leu Leu Arg Gln Lys Leu Gly Ser Lys Ser Val Val His
65                  70                  75                  80

Arg Asp Ala Gly Ala Met Cys Ala Asp Leu Leu Val Thr Asp Gly Val
                85                  90                  95

Pro Leu Gln Val Gly Asp Leu Glu Leu Glu Val Arg His Thr Pro Gly
            100                 105                 110

His Thr Asn Gly Cys Val Ser Tyr Val Met Ala Asp Arg Val Phe Thr
        115                 120                 125

Gly Asp Ala Leu Leu Ile Gly Gly Ser Gly Arg Thr Asp Phe Gln Gln
    130                 135                 140

Gly Asp Ala Gly Gln Leu Tyr Asp Ser Ile Thr Gly Lys Leu Phe Thr
145                 150                 155                 160

Leu Pro Pro Asp Thr Leu Val Tyr Pro Gly His Asp Tyr Asn Gly Asn
                165                 170                 175

Thr Val Ser Thr Ile Lys Gln Glu Met Ala Lys Asn Thr Arg Leu Gly
            180                 185                 190

Gly Gly Lys Ser Arg Glu Glu Phe Ile Ala Ile Leu Gln Asp Leu Lys
        195                 200                 205

Leu Ala Tyr Pro Lys Phe Ile Asp Lys Ala Leu Pro Ala Asn Gln Ser
    210                 215                 220

Cys Gly Leu Ile Ala Gln Gly
225                 230
```

<210> SEQ ID NO 9
<211> LENGTH: 579
<212> TYPE: DNA
<213> ORGANISM: Methylomonas sp. 16a
<220> FEATURE:
<221> NAME/KEY: misc_feature
<222> LOCATION: (424)..(426)
<223> OTHER INFORMATION: ATG start site of glyoxalase gene

<400> SEQUENCE: 9

```
gcctgctttg gactgatcga tagcttacgg cttaccccca agtcatgca tgaaccctgt       60 cgatgatgtc atcggtggac aacccaaacg atctccccct cctgtcgcaa caaagcttcg     120
ccatcggcct cggaccgcgc cggcatcgac tcattcaaaa agcttgagcc ttggtaaaag     180
tcgattgtat taagccagca tttgcaatga ctcatggcta gagccaccaa atgtttcaca     240
aacatttcaa atgaaacaca atcgtttcaa cacttcagcc tgaaacaacc gagaaacaaa    300
```

-continued

```
cacttgaaaa agaagcagca aaatcaatac ataagcgcgt ggcaaggcct aaaaaaactg      360
gcacgggaat tgatataaga acatcaagct tttctaattt ttgttaaaac caggagccta      420
gtcatgattt tcaagcaact tttcgaaacc gaaacatcga cctatagcta tttgctgggc      480
tgtgaacgca ctcaccgcgc gattttaatc gatccggtcg cctcggaact ggatgactat      540
atcgatctgt tgaatagcct gactctcaaa ttgatttat                             579
```

<210> SEQ ID NO 10
<211> LENGTH: 1932
<212> TYPE: DNA
<213> ORGANISM: Methylomonas sp. 16a

<400> SEQUENCE: 10

```
atgactgttg aagcaaaaaa agaaaccttg ggctttcaaa ccgaagtgaa gcatctgttg      60
catttgatga ttcactcgct atacagcaac aaggaaatct tcctgcgcga attgatttcc     120
aacgcctccg acgccgccga caaactgcgc ttcgaagcgc tggccaacga cagcctgtac     180
gaaggcgaca gcgaattgaa atccgcgtc gatttcgacg aagcaaaaaa aaccatcacc      240
atcaccgata acggcatcgg catgagccgt gaggaagtgc aggaccatat cggcaccatc     300
gccaaatccg gcaccaagca attcttcgaa aaattgaccg gcgaccaggc caaggacagc     360
gagctgatcg gccagttcgg tgtcggtttt tattcggcct tcatcgtcgc cgacaaagtc     420
acgctgacga cccgcaaggc cggcgcgccg catgaccaag gcgtgcgctg ggaatccgac     480
ggcctgggcg aatacagcat cgaaaccgtc gaaaaagctg gtcgcggcac cgaaatcgtg     540
ctgcatctga agaaggcga agacgatttc ctgagcagct ggaagctacg ttccatcatc     600
aagaaatact ccgaccacat ctctttgccc atcatcatga gcaaggaaat cccggccgag     660
aaggacgacg acggcaacga aaccgcgccg gcccgtgtcg aagacgaaac cgtcaacagc     720
gcctcggcct tgtggacaaa atccaaggac gacatcagcg cggaacagta caacgagttt     780
tacaaacacg tcgcccacga cttccaggac ccgctggttc acgttcatag caaagtcgaa     840
ggcaccaacg aatacacctt gttgctgtac gtccccggcc gggcgccgtt tgatttgtgg     900
gaccgcgacg ccaaacacgg cgtcaagctg tacatcaaga agtcttcat caccgacgac     960 gccgaacaac tgatgccgcg ctacctgcgc ttcgtgcgcg gtatcgtcga tgccgacagc    1020
ttgccgctga acgtatcacg ggaaatcctg caacaaagca agcaaatcag cgcgatcaaa    1080
tccggcgcgg tgaaaaaagt gctgggcatg ctggaagaca tggccgagaa cgacgtcgag    1140
aaataccaaa aattctggga acagttcggc aacgtcatca aggaaggccc gatagaagac    1200
cacaaaaaca aagatcgcat cgccaacctg ttgcgtttct cgtcaaccca tagcgacgac    1260
aaaacccaaa acgtgtcgct ggccgattat gtcagtcgac tgaaggaagg ccagaacaaa    1320
atctacttca tcaccgccga tagctatgcg gcggccaaaa acagcccgca tctggaagtg    1380
ttccgcaaaa aaggcctgga agtgttgctg ctgaccgacc gcatcgacga atggctggtg    1440
tccagcctga ccgaattcga cggcaagcac atgcaatcga tcgccaaagg cgaactggac    1500
ctggacaaat cgacagcga agaagagaaa aacaccagg aagaagtcag caaagacttc    1560
gaatcggtcg tcaagcaaat ccaggaagtg ctgaaagaca aagtcagcga agtgaaaatc    1620
agccaccgcc tgaccgactc gccagccgt ctggtgaccg cgccctacga catgagcctg    1680
cacatggagc gcatcatgaa ggaagccggc cacgccatga acatgatggg catgggcggc    1740
agcaagccga tcttcgaaat caacccggac cacgccatcg tccaggccct gaaaaacgag    1800
caagacgaca cccgcttcgc cgacattagt cacatcctgt tcgatcaggc catcctcagc    1860
```

```
gaaggcggcc aactggacga cccggcggcg ttcgtgcata agctgaatgg cttgttgcaa   1920
ggtctactga ag                                                      1932
```

<210> SEQ ID NO 11
<211> LENGTH: 644
<212> TYPE: PRT
<213> ORGANISM: Methylomonas sp. 16a

<400> SEQUENCE: 11

```
Met Thr Val Glu Ala Lys Lys Glu Thr Leu Gly Phe Gln Thr Glu Val
1               5                   10                  15

Lys His Leu Leu His Leu Met Ile His Ser Leu Tyr Ser Asn Lys Glu
            20                  25                  30

Ile Phe Leu Arg Glu Leu Ile Ser Asn Ala Ser Asp Ala Ala Asp Lys
        35                  40                  45

Leu Arg Phe Glu Ala Leu Ala Asn Asp Ser Leu Tyr Glu Gly Asp Ser
    50                  55                  60

Glu Leu Lys Ile Arg Val Asp Phe Asp Glu Ala Lys Lys Thr Ile Thr
65                  70                  75                  80

Ile Thr Asp Asn Gly Ile Gly Met Ser Arg Glu Val Gln Asp His
                85                  90                  95

Ile Gly Thr Ile Ala Lys Ser Gly Thr Lys Gln Phe Glu Lys Leu
            100                 105                 110

Thr Gly Asp Gln Ala Lys Asp Ser Glu Leu Ile Gly Gln Phe Gly Val
        115                 120                 125

Gly Phe Tyr Ser Ala Phe Ile Val Ala Asp Lys Val Thr Leu Thr Thr
    130                 135                 140

Arg Lys Ala Gly Ala Pro His Asp Gln Gly Val Arg Trp Glu Ser Asp
145                 150                 155                 160

Gly Leu Gly Glu Tyr Ser Ile Glu Thr Val Glu Lys Ala Gly Arg Gly
                165                 170                 175

Thr Glu Ile Val Leu His Leu Lys Glu Gly Glu Asp Asp Phe Leu Ser
            180                 185                 190

Ser Trp Lys Leu Arg Ser Ile Ile Lys Lys Tyr Ser Asp His Ile Ser
        195                 200                 205

Leu Pro Ile Ile Met Ser Lys Glu Ile Pro Ala Glu Lys Asp Asp
    210                 215                 220

Gly Asn Glu Thr Ala Pro Ala Arg Val Glu Asp Glu Thr Val Asn Ser
225                 230                 235                 240

Ala Ser Ala Leu Trp Thr Lys Ser Lys Asp Asp Ile Ser Ala Glu Gln
                245                 250                 255

Tyr Asn Glu Phe Tyr Lys His Val Ala His Asp Phe Gln Asp Pro Leu
            260                 265                 270

Val His Val His Ser Lys Val Glu Gly Thr Asn Glu Tyr Thr Leu Leu
        275                 280                 285

Leu Tyr Val Pro Gly Arg Ala Pro Phe Asp Leu Trp Asp Arg Asp Ala
    290                 295                 300

Lys His Gly Val Lys Leu Tyr Ile Lys Lys Val Phe Ile Thr Asp Asp
305                 310                 315                 320

Ala Glu Gln Leu Met Pro Arg Tyr Leu Arg Phe Val Arg Gly Ile Val
                325                 330                 335

Asp Ala Asp Ser Leu Pro Leu Asn Val Ser Arg Glu Ile Leu Gln Gln
            340                 345                 350
```

```
Ser Lys Gln Ile Ser Ala Ile Lys Ser Gly Ala Val Lys Val Leu
        355                 360                 365
Gly Met Leu Glu Asp Met Ala Glu Asn Asp Val Glu Lys Tyr Gln Lys
    370                 375                 380
Phe Trp Glu Gln Phe Gly Asn Val Ile Lys Glu Gly Pro Ile Glu Asp
385                 390                 395                 400
His Lys Asn Lys Asp Arg Ile Ala Asn Leu Leu Arg Phe Ser Ser Thr
            405                 410                 415
His Ser Asp Asp Lys Thr Gln Asn Val Ser Leu Ala Asp Tyr Val Ser
        420                 425                 430
Arg Met Lys Glu Gly Gln Asn Lys Ile Tyr Phe Ile Thr Ala Asp Ser
    435                 440                 445
Tyr Ala Ala Lys Asn Ser Pro His Leu Glu Val Phe Arg Lys Lys
450                 455                 460
Gly Leu Glu Val Leu Leu Leu Thr Asp Arg Ile Asp Glu Trp Leu Val
465                 470                 475                 480
Ser Ser Leu Thr Glu Phe Asp Gly Lys His Met Gln Ser Ile Ala Lys
            485                 490                 495
Gly Glu Leu Asp Leu Asp Lys Phe Asp Ser Glu Glu Lys Lys His
        500                 505                 510
Gln Glu Glu Val Ser Lys Asp Phe Glu Ser Val Val Lys Gln Ile Gln
    515                 520                 525
Glu Val Leu Lys Asp Lys Val Ser Glu Val Lys Ile Ser His Arg Leu
530                 535                 540
Thr Asp Ser Pro Ala Cys Leu Val Thr Gly Ala Tyr Asp Met Ser Leu
545                 550                 555                 560
His Met Glu Arg Ile Met Lys Glu Ala Gly His Ala Met Asn Met Met
            565                 570                 575
Gly Met Gly Gly Ser Lys Pro Ile Phe Glu Ile Asn Pro Asp His Ala
        580                 585                 590
Ile Val Gln Ala Leu Lys Asn Glu Gln Asp Asp Thr Arg Phe Ala Asp
    595                 600                 605
Ile Ser His Ile Leu Phe Asp Gln Ala Ile Leu Ser Glu Gly Gly Gln
610                 615                 620
Leu Asp Asp Pro Ala Ala Phe Val His Lys Leu Asn Gly Leu Leu Gln
625                 630                 635                 640
Gly Leu Leu Lys

<210> SEQ ID NO 12
<211> LENGTH: 650
<212> TYPE: DNA
<213> ORGANISM: Methylomonas sp. 16a
<220> FEATURE:
<221> NAME/KEY: misc_feature
<222> LOCATION: (541)..(543)
<223> OTHER INFORMATION: ATG start site of heat shock protein (htpg) gene

<400> SEQUENCE: 12
tacgttggtg ctatatgtgc tctgactgcc gtcaaccgtc acctgccagc ctgctggaac      60
attgcctttg ccgtttttga cattaccggt gatgttgcct ttgccgtaag acagcagtgt     120
atcggcgtca ttgtcgctac cggaaaagaa actggtcgaa tcaaaggtaa aggttcgggt     180
ggcgtccgcg atatccgtcg tgtaagcaaa tgccgaacta cttgcgcagc tcatcgcaaa     240
aagtaatgcc gttatggact tggttttcat ctttgttttt ctcctttttga aacaagattg    300 cgccatagtc tactgattca accaaacgcg aactattgcc aatagtatg aatgattttt       360
```

```
gcgttgaaat cgcggcgatt ctcctagggc aggttagcta tttcagagaa tgggtcagat      420
ttgtttacgg gcagagcggg aatcgtgtaa tccatcggct tttttaaatg tggccttgaa      480
aaacgccagt gctatcccca aatcgcagca gtccgatttt aactttcaa gagaccacac       540 atgactgttg aagcaaaaaa agaaacctta ggctttcaaa ccgaagtgaa gcatctgttg      600
catttgatga ttcactcgct atacagcaac aaggaaatct tcctgcgcga                 650

<210> SEQ ID NO 13
<211> LENGTH: 267
<212> TYPE: DNA
<213> ORGANISM: Methylomonas sp. 16a

<400> SEQUENCE: 13
atgatcaaca aagctggttt tcaacgacta attctgatct tcaggtcgcg cctcacttat       60
agcgataaaa atcctggagg aaacatgcaa caactcgatt tgcgcatagt cgggaaaacc      120
gcggccttgt tggctggtgg ccttctgagc gtggcgcaac ccgcatcggc gaacaaggag      180
ctggaacagc tctccaagca aaacaccaac tgggtcatgc aaaccaaaga ttacgcatcg      240
acccatttca gcgaaatgat cgacatc                                          267

<210> SEQ ID NO 14
<211> LENGTH: 89
<212> TYPE: PRT
<213> ORGANISM: Methylomonas sp. 16a

<400> SEQUENCE: 14

Met Ile Asn Lys Ala Gly Phe Gln Arg Leu Ile Leu Ile Phe Arg Ser
1               5                   10                  15

Arg Leu Thr Tyr Ser Asp Lys Asn Pro Gly Gly Asn Met Gln Gln Leu
            20                  25                  30

Asp Leu Arg Ile Val Gly Lys Thr Ala Ala Leu Leu Ala Gly Gly Leu
        35                  40                  45

Leu Ser Val Ala Gln Pro Ala Ser Ala Asn Lys Glu Leu Glu Gln Leu
    50                  55                  60

Ser Lys Gln Asn Thr Asn Trp Val Met Gln Thr Lys Asp Tyr Ala Ser
65                  70                  75                  80

Thr His Phe Ser Glu Met Ile Asp Ile
                85

<210> SEQ ID NO 15
<211> LENGTH: 696
<212> TYPE: DNA
<213> ORGANISM: Methylomonas sp. 16a
<220> FEATURE:
<221> NAME/KEY: misc_feature
<222> LOCATION: (501)..(503)
<223> OTHER INFORMATION: ATG start site of methanol dehydrogenase
                        (moxF) gene

<400> SEQUENCE: 15
gcgccgtatg ctttcgaatc cgccaagacc gggcatggat aaatccatga ccaccacatc       60
gggcaattgc tttgaataga gttggcaagc ggtctcgcca cgatcggctt catagatctc      120
gccgatacga tccgacagcg atagataggt cttgtagccg gtacgaacca cggcgtgatc      180
atctaccaat aaaacgctga tttactcgc cactggaaaa ttcctcctc aggtcgtcaa       240 gggataaaga tatgggacaa gtccagtctg atgccaggcg acttggtgt gccttttttt       300 atgatgacgc tttatccgtg cttaaaccat gggagctttt cccgtttcca atttcgatcc      360
```

-continued

```
ttggcgagat aggaatattt ccgtgcatga ttgcgtcgat ttcacatcga tttcatggat    420
tgttccgtaa cgttagccag cccggcttct ataacatttg cgccagcgtg gcctggtggt    480
cggtaacccg tgatgcggtt atgatcaaca agctggtttt caacgactaa attctgatct    540
tcaggtcgcg cctcacttat agcgataaaa atcctggagg aaacatgcaa caactcgatt    600
tgcgcatagt cgggaaaacc gcggccttgt tggctggtgg ccttctgagc gtggcgcaac    660
ccgcatcggc gaacaaggag ctggaacagc tctcca                             696
```

<210> SEQ ID NO 16
<211> LENGTH: 645
<212> TYPE: DNA
<213> ORGANISM: Methylomonas sp. 16a

<400> SEQUENCE: 16

```
atggcaagac cattaattca atggcgttg gattcactgg atttcgacca aaccgtggca    60
ttggcggatc aagtggcgcc atatgtggat atttttgaaa tcggtacccc ttgcatcaaa    120
tacaacggta tcaacctggt taaagcgttg agagaacgtt accctgacaa actgttgctg    180
gttgacctga aaccatgga cgctggcgaa tacgaagccg gtgcattcta tgccgctggt    240
gccgacatct gcaccgtatt gggtgtgtct ggtctggcta ccatcggtgg cgtcatcaag    300
gctgcgaaaa acacgcggc cgaagttcaa gttgacctga tcaacgtgcc gaacaaagca    360
gagtgcgcac gcgaatctgc aaaattgggc gcgcaaatca tgggcgttca caccggtctg    420
gacgcgcaag ccgcgggtca aaccccattt accgacctga tgaagttgc ctccttgggc    480 ttgaacgttc gtgtttctgt tgctggcggt atcaaacctg cgactattga tcaaaccgtt    540
aaagcgggcg caaacatcat cgttgtcggc gcagcgatct acggtgcgcc gtcacctgcc    600
gaagcagcgc gtgaaattcg tgaattggta gaagcagcag cggta                   645
```

<210> SEQ ID NO 17
<211> LENGTH: 215
<212> TYPE: PRT
<213> ORGANISM: Methylomonas sp. 16a

<400> SEQUENCE: 17

```
Met Ala Arg Pro Leu Ile Gln Met Ala Leu Asp Ser Leu Asp Phe Asp
1               5                   10                  15

Gln Thr Val Ala Leu Ala Asp Gln Val Ala Pro Tyr Val Asp Ile Phe
            20                  25                  30

Glu Ile Gly Thr Pro Cys Ile Lys Tyr Asn Gly Ile Asn Leu Val Lys
        35                  40                  45

Ala Leu Arg Glu Arg Tyr Pro Asp Lys Leu Leu Leu Val Asp Leu Lys
    50                  55                  60

Thr Met Asp Ala Gly Glu Tyr Glu Ala Gly Ala Phe Tyr Ala Ala Gly
65                  70                  75                  80

Ala Asp Ile Cys Thr Val Leu Gly Val Ser Gly Leu Ala Thr Ile Gly
                85                  90                  95

Gly Val Ile Lys Ala Ala Lys Lys His Ala Ala Glu Val Gln Val Asp
            100                 105                 110

Leu Ile Asn Val Pro Asn Lys Ala Glu Cys Ala Arg Glu Ser Ala Lys
        115                 120                 125

Leu Gly Ala Gln Ile Met Gly Val His Thr Gly Leu Asp Ala Gln Ala
    130                 135                 140

Ala Gly Gln Thr Pro Phe Thr Asp Leu Asn Glu Val Ala Ser Leu Gly
```

```
                         145                 150                 155                 160
Leu Asn Val Arg Val Ser Val Ala Gly Gly Ile Lys Pro Ala Thr Ile
                     165                 170                 175

Asp Gln Thr Val Lys Ala Gly Ala Asn Ile Ile Val Gly Ala Ala
                 180                 185                 190

Ile Tyr Gly Ala Pro Ser Pro Ala Glu Ala Ala Arg Glu Ile Arg Glu
             195                 200                 205

Leu Val Glu Ala Ala Ala Val
        210                 215

<210> SEQ ID NO 18
<211> LENGTH: 500
<212> TYPE: DNA
<213> ORGANISM: Methylomonas sp. 16a
<220> FEATURE:
<221> NAME/KEY: misc_feature
<222> LOCATION: (210)..(212)
<223> OTHER INFORMATION: ATG start site of 3-hexulose-6-phosphate
                        synthase (hmps) gene

<400> SEQUENCE: 18
ttcggaatcc ctgacgggaa ttggcccgaa gaaggcagat gccatcgttc agtatcgaaa      60
ggaacatggg gattttcagt cattgaagga tctggagaat gtcagcggca ttggcgagaa     120
aacccttcag gccaatgaaa aagacattcg cttcacggat gatttgagcg ataagtcatc     180
cgcggaaaaa ggtgcggtag ctgtggataa aaaaggcgcc agatagtaag cgctaaggat     240
tggggtgcgt cgccggtcgc ggcggcgctc ctcgacggca gagttggtgc caggttggcg     300
gatgattgat gccgaatatt acgcgaccaa ttctcgaggc aaatgaactg tgagctactg     360
agttgcaggc attgacagcc atcccatttc tatcatacag ttacgacgc atcacgagta      420 ggtgataagc ctagcagatt gcggcagttg gcaaaatcag ctattactaa taattaaaaa     480
ctttcggagc acatcacatg                                                  500

<210> SEQ ID NO 19
<211> LENGTH: 32
<212> TYPE: DNA
<213> ORGANISM: Methylomonas sp. 16a

<400> SEQUENCE: 19
caggatccgc gccgtatgct ttcgaatccg cc                                     32

<210> SEQ ID NO 20
<211> LENGTH: 34
<212> TYPE: DNA
<213> ORGANISM: Methylomonas sp. 16a

<400> SEQUENCE: 20
caggatcctg gagagctgtt ccagctcctt gttc                                   34

<210> SEQ ID NO 21
<211> LENGTH: 22
<212> TYPE: DNA
<213> ORGANISM: Methylomonas sp. 16a

<400> SEQUENCE: 21
cccatgggtt cggaatccct ga                                                22

<210> SEQ ID NO 22
<211> LENGTH: 35
<212> TYPE: DNA
```

-continued

```
<213> ORGANISM: Methylomonas sp. 16a

<400> SEQUENCE: 22
ggaattcctc ctctccgaaa gtttttaatt attag                              35

<210> SEQ ID NO 23
<211> LENGTH: 27
<212> TYPE: DNA
<213> ORGANISM: Pantoea stweartii

<400> SEQUENCE: 23
cggaattccc gccctgccac tcatcgc                                       27

<210> SEQ ID NO 24
<211> LENGTH: 51
<212> TYPE: DNA
<213> ORGANISM: Pantoea stweartii

<400> SEQUENCE: 24
ccagaatgag atcatagtgc ggttgcatgc agcatcctta actgacggca g            51

<210> SEQ ID NO 25
<211> LENGTH: 51
<212> TYPE: DNA
<213> ORGANISM: Pantoea stweartii

<400> SEQUENCE: 25
ctgccgtcag ttaaggatgc tgcatgcaac cgcactatga tctcattctg g            51

<210> SEQ ID NO 26
<211> LENGTH: 33
<212> TYPE: DNA
<213> ORGANISM: Pantoea stweartii

<400> SEQUENCE: 26
gcgaattcgc tagcggctag atcgggcgct gcc                                33
```

NATURAL PROMOTERS FOR GENE EXPRESSION IN C1 METABOLIZING BACTERIA

FIELD OF THE INVENTION

Figure 1:
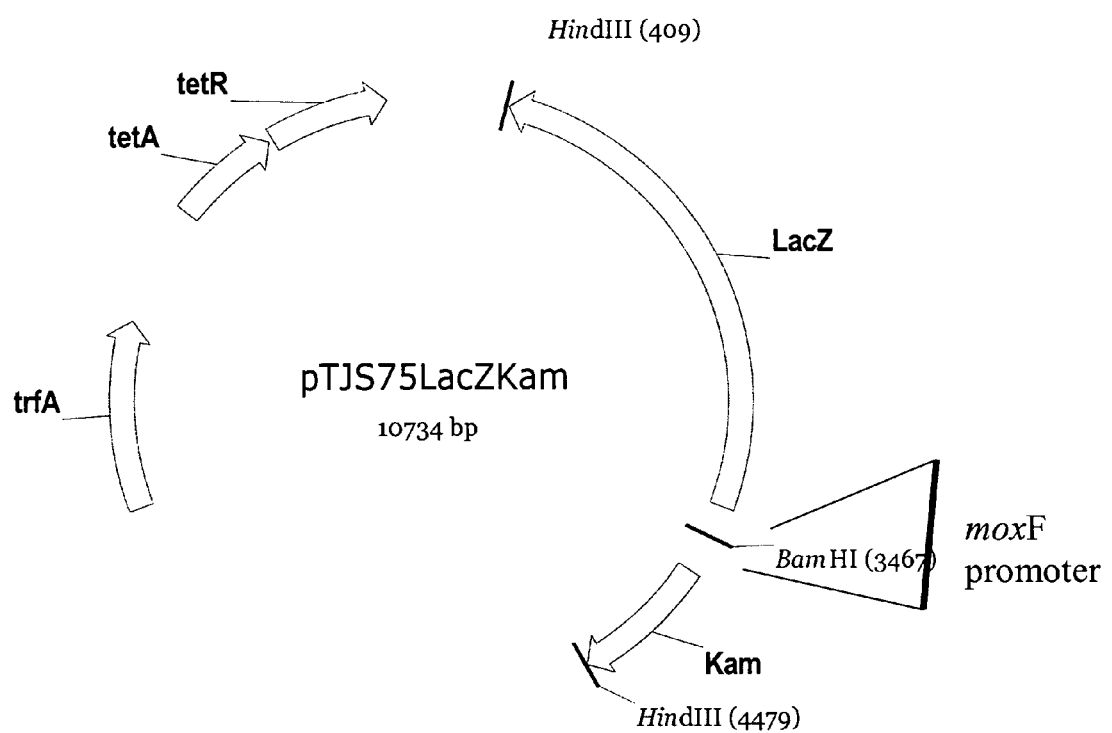

This invention is in the field of bacterial gene expression and metabolic engineering. More specifically, the invention relates to the use of promoter regions isolated from a *Methylomonas* sp. for gene expression in C1 metabolizing bacteria.

BACKGROUND INFORMATION

Methanotrophic bacteria are defined by their ability to use methane as their sole source of carbon and energy under ambient conditions. This ability, in conjunction with the abundance of methane, makes the biotransformation of methane a potentially unique and valuable process. As such, several approaches have been used in attempts to harnesss the unique natural abilities of these organisms for commercial applications.

Historically, the commercial applications of biotransformation of methane have fallen broadly into three categories:
1) Production of single cell protein (Sharpe D. H. Bio-Protein Manufacture (1989). Ellis Horwood series in applied science and industrial technology. New York: Halstead Press) (Villadsen, John, *Recent Trends Chem. React. Eng.*, [Proc. Int. Chem. React. Eng. Conf.], 2nd (1987), Volume 2, pp 320–33. Editor(s): Kulkarni, B. D.; Mashelkar, R. A.; Sharma, M. M. Publisher: Wiley East., New Delhi, India; Naguib, M., Proc. OAPEC Symp. Petroprotein, [Pap.] (1980), Meeting Date 1979, pp 253–77 Publisher: Organ. Arab Pet. Exporting Countries, Kuwait, Kuwait);
2) Epoxidation of alkenes for production of chemicals (U.S. Pat. No. 4,348,476); and
3) Biodegradation of chlorinated pollutants (Tsien et al., *Gas, Oil, Coal, Environ. Biotechnol.* 2, [Pap. Int. IGT Symp. *Gas, Oil, Coal, Environ. Biotechnol.*], 2nd (1990), pp 83–104. Editor(s): Akin, Cavit; Smith, Jared. Publisher: Inst. Gas Technol., Chicago, Ill.; WO 9,633,821; Merkley et al., *Biorem. Recalcitrant Org.*, [Pap. Int. In Situ On-Site Bioreclam. Symp.], 3rd (1995), pp. 165–74. Editor(s): Hinchee, Robert E; Anderson, Daniel B.; Hoeppel, Ronald E. Publisher: Battelle Press, Columbus, Ohio; Meyer et al., *Microb. Releases* 2(1): 11–22 (1993)).

Epoxidation of alkenes has experienced only slight commercial success due to low product yields, toxicity of products and the large amount of cell mass required to generate products.

Large-scale protein production from methane, termed single cell protein or SCP, has been technically feasible and commercialized at large scale (Villadsen, supra). Single cell protein is a relatively low value product. As such, the economic production cannot tolerate heavy bioprocessing costs. The yield of the methanotrophic strain used for producing SCP may be critical to the overall economic viability of the process. Microbial biomass produced by methanotrophic bacteria is typically very high in protein content (~70–80% by weight), which can restrict the direct use of this protein to certain types of animal feed.

In addition to the synthesis of SCP, methanotrophic cells can further build the oxidation products of methane (i.e. methanol and formaldehyde) into complex molecules such as carbohydrates and lipids. For example, under certain conditions methanotrophs are known to produce exopolysaccharides (WO 02/20797; WO 02/20728; Ivanova et al., *Mikrobiologiya* 57(4):600-5 (1988); Kilbane, John J., II *Gas, Oil, Coal, Environ. Biotechnol.* 3, [Pap. IGT's Int. Symp.], 3rd (1991), Meeting Date 1990, pp. 207–26. Editor(s): Akin, Cavit; Smith, Jared. Publisher: IGT, Chicago, Ill.). Similarly, methanotrophs are known to accumulate both isoprenoid compounds and carotenoid pigments of various carbon lengths (WO 02/20733; WO 02/20728; Urakami et al., *J. Gen. Appl. Microbiol.* 32(4):317–41 (1986)).

Most recently, the natural abilities of methanotrophic organisms have been stretched by the advances of genetic engineering. Odom et al. have investigated *Methyolomonas* sp. 16a as a microbial platform of choice for production of a variety of materials beyond single cell protein including carbohydrates, pigments, terpenoid compounds and aromatic compounds (WO 02/20728; WO 02/18617). This particular methanotrophic bacterial strain is capable of efficiently using either methanol or methane as a carbon substrate, is metabolically versatile in that it contains multiple pathways for the incorporation of carbon from formaldehyde into 3-carbon units, and is amenable to genetic engineering via bacterial conjugation using donor species such as *Escherichia coli*. Thus, *Methyolomonas* sp. 16a can be engineered to produce new classes of products other than those naturally produced from methane. Further advancement in the metabolic engineering of methanotrophs such as *Methyolomonas* sp. 16a, however, is currently limited by the lack of a detailed understanding of promoters useful to drive the expression of foreign and native genes in this host. Additionally, it would be useful to possess a suite of promoters that are individually regulatable under a variety of natural growth and induction conditions.

In general, prokaryotic promoters can play an important role in biotechnology, particularly for directing expression of chimeric genes to alter cellular metabolism to produce larger quantities of a natural productor new products. Producing high levels of a specific protein may also be desirable as a product. Promoters that are generally used for gene expression in *E. coli* may not be suitable for driving chimeric gene expression in *Methylomonas*, especially when a strong or inducible promoter is required. Promoters that are strong in *E. coli*, generally have much lower expression levels in *Methylomonas*. Induction systems used with inducible promoters in *E. coli* generally do not function well in *Methylomonas*.

The problem to be solved therefore is to provide promoters that are useful for expression of chimeric genes under desired conditions in *Methylomonas*. Promoters with high expression during growth on methane and methanol are valuable when *Methylomonas* is used as a production host. Similarly, promoters induced by growth on nitrate and by change in temperature and pH conditions are very applicable in industrial settings, as each of these conditions can be adjusted easily. Applicants have solved the stated problem by identifying genes within the *Methylomonas* sp. 16a genome that are regulated by designated metabolic and growth conditions, and isolating the promoters from these genes. The nucleic acid sequences of the genes can be used for bioreactor monitoring in *Methylomonas* sp. and C1 metabolizing bacterial cultures. Specifically, applicants have used microarray technology to identify genes that are responsive to: 1.) growth on methane and methanol; 2.) induction in the presence of nitrate; 3.) induction by change in growth temperature; and 4.) induction by modification of media pH. Homologs of these genes should be useful for similar purposes in a variety of C1 metabolizing bacteria.

SUMMARY OF THE INVENTION

The invention relates to new promoter regions isolated from inducible genes isolated from a species of *Methylomonas* designated herein as *Methylomonas* 16a. The promoter regions are derived from; a nitrogen transporter gene (nrtA) and a nitrogen regulating protein (glnB), both inducible by nitrate; a heat shock protein encoding gene (htpB), inducible at elevated temperature; a methanol dehydrogenaase gene (moxF) and a hexulose-6-phosphate syntase (hps) both highly expressed in the presence of methanol or methane. Theses promoter regions have been found to be effective for drivign the expression of a variety of coding regions in C1 metabolizing bacteria.

Accordingly the invention provides a method for the expression of a coding region of interest in a C1 metabolizing bacteria comprising:
 a) providing a transformed C1 metabolizing bacterial cell having a chimeric gene comprising;
  1) a promoter region of a gene selected from the group consisting of: a nrtA gene and a glnB gene; and
  2) a coding region of interest expressible in a C1 metabolizing bacteria;
 wherein the promoter region is operably linked to a coding region of interest; and
 b) growing the transformed C1 metabolizing bacteria cell of step (a) in the presence of nitrate wherein the chimeric gene is expressed.

Similarly the invention provides a method for the expression of a coding region of interest in a C1 metabolizing bacteria comprising:
 a) providing a transformed C1 metabolizing bacterial cell having a chimeric gene comprising;
  1) a promoter region of a glyoxll gene; and
  2) a coding region of interest expressible in a C1 metabolizing bacteria;
 wherein the promoter region is operably linked to a coding region of interest; and
 b) growing the transformed C1 metabolizing bacteria cell of step (a) at a pH of about 5.5 wherein the chimeric gene is expressed.

In an alternate embodiment the invention provides a method for the expression of a coding region of interest in a C1 metabolizing bacteria comprising:
 a) providing a transformed C1 metabolizing bacterial cell having a chimeric gene comprising;
  1) a promoter region of a htpG gene; and
  2) a coding region of interest expressible in a C1 metabolizing bacteria;
 wherein the promoter region is operably linked to a coding region of interest; and
 b) growing the transformed C1 metabolizing bacteria cell of step (a) at a temperature suitable for induction of the promoter region wherein the chimeric gene is expressed.

In another embodiment the invention provides a method for the expression of a coding region of interest in a C1 metabolizing bacteria comprising:
 a) providing a transformed C1 metabolizing bacterial cell having a chimeric gene comprising;
  1) a promoter region of a gene selected from the group consisting of: a moxF gene and a hps gene; and
  2) a coding region of interest expressible in a C1 metabolizing bacteria;
 wherein the promoter region is operably linked to a coding region of interest; and
 b) growing the transformed C1 metabolizing bacteria cell of step (a) in the presence of a C1 carbon source selected from the group consisting of methane and methanol wherein the chimeric gene of step (a) is expressed.

Preferred hosts for expression the promoter regions of the invention are methanotrophs and methylotrophs.

Preferred coding regions for expression under the control of the promoter regions of the invention are those involved in the biosynthesis of carotenoids.

The invention additionally provides an isolated nucleic acid molecule encoding a nitrate inducible gene selected from the group consisting of:
 (a) an isolated nucleic acid molecule encoding the amino acid sequence selected from the group consisting of SEQ ID NO:2 and SEQ ID NO:5;
 (b) an isolated nucleic acid molecule that hybridizes with (a) under stringent conditions and is washed with 0.1×SSC, 0.1% SDS, 65° C.; or
 an isolated nucleic acid molecule that is complementary to (a), or (b).

Similarly the invention provides an isolated nucleic acid molecule encoding a pH inducible gene selected from the group consisting of:
 a) an isolated nucleic acid molecule encoding the amino acid sequence as set forth in SEQ ID NO:8;
 b) an isolated nucleic acid molecule that hybridizes with (a) under stringent conditions and is washed with 0.1×SSC, 0.1% SDS, 65° C.; or
 an isolated nucleic acid molecule that is complementary to (a), or (b).

In another embodiment the invention provides an isolated nucleic acid molecule encoding a temperature inducible gene selected from the group consisting of:
 a) an isolated nucleic acid molecule encoding the amino acid sequence as set forth in SEQ ID NO:11;
 b) an isolated nucleic acid molecule that hybridizes with (a) under stringent conditions and is washed with 0.1×SSC, 0.1% SDS, 65° C.; or an isolated nucleic acid molecule that is complementary to (a), or (b).

Similarly the invention provides an isolated nucleic acid molecule encoding a methane or methanol inducible gene selected from the group consisting of:
 (a) an isolated nucleic acid molecule encoding the amino acid sequence selected from the group consisting of SEQ ID NO:14, and 17;
 (b) an isolated nucleic acid molecule that hybridizes with (a) under stringent conditions and is washed with 0.1×SSC, 0.1% SDS, 65° C.; or an isolated nucleic acid molecule that is complementary to (a), or (b).

In specific embodiments the invention provides promoter regions isolated from the subject genes having the nucleic acid sequences as set forth in SEQ ID NO:3 and SEQ ID NO:6, SEQ ID NO:9, SEQ ID NO:12, SEQ ID NO:15, and SEQ ID NO:18.

In addition to the nucleic acids of the invention, the invention provides polypeptides encoded thereby, chimeric genes comprising the nucleic acids of the invention, and host cells transformed therewith.

BRIEF DESCRIPTION OF THE FIGURES, SEQUENCE DESCRIPTIONS, AND BIOLOGICAL DEPOSITS

FIG. 1 is a plasmid map of pTJS75LacZKam with insertion of the moxF promoter drawn.

Figure 2:
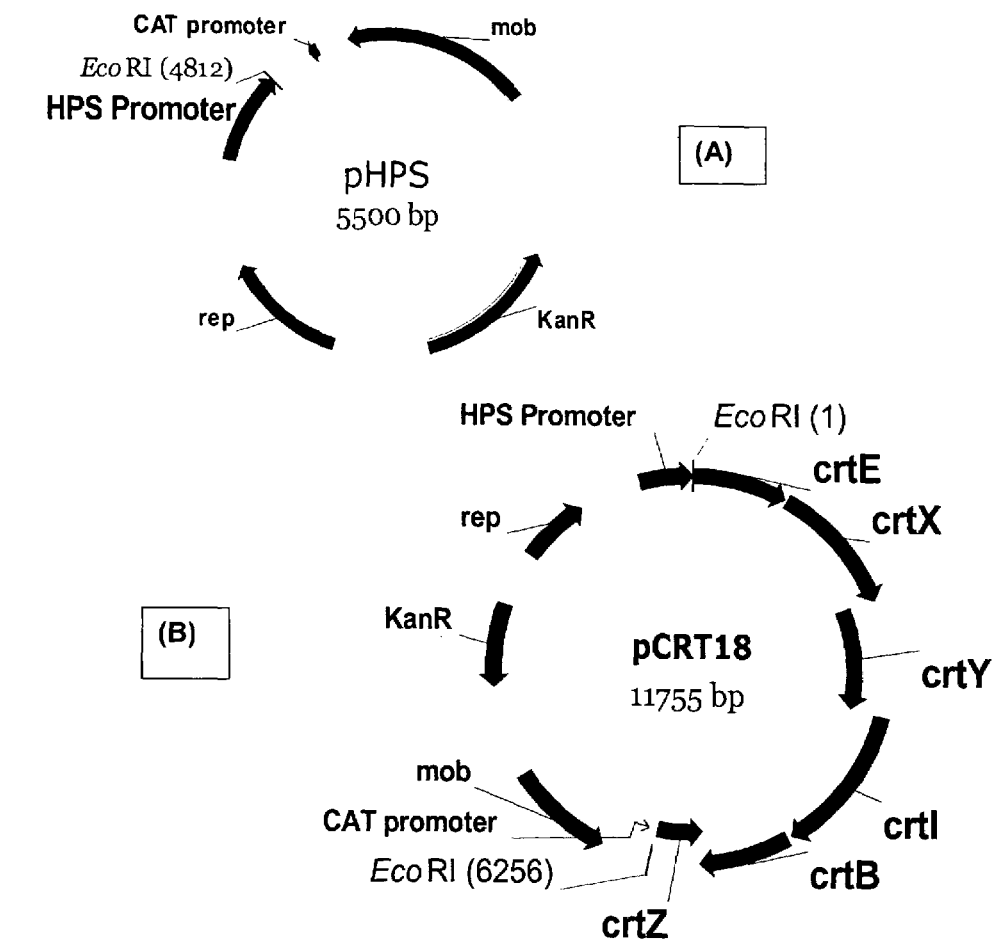

FIG. 2A schematically illustrates the plasmid map of pHPS, while FIG. 2B is a plasmid map for pCRT18. FIG. 2C shows HPLC results demonstrating the presence of zeaxanthin glucosides in Methylomonas cells transformed with pCRT18.

Figure 3:
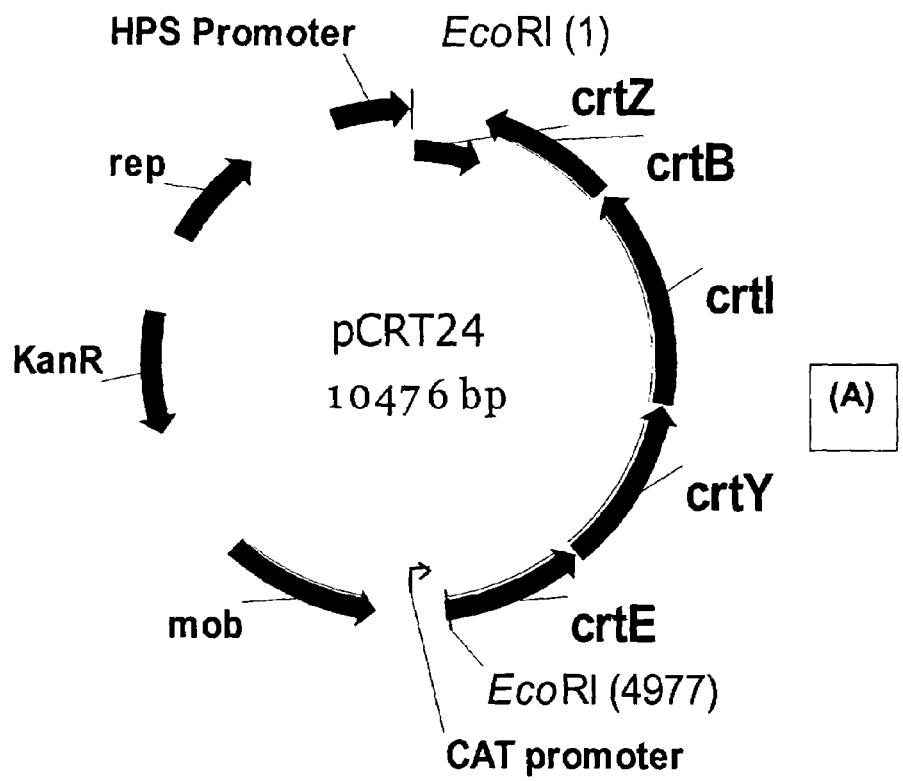
Figure 3:
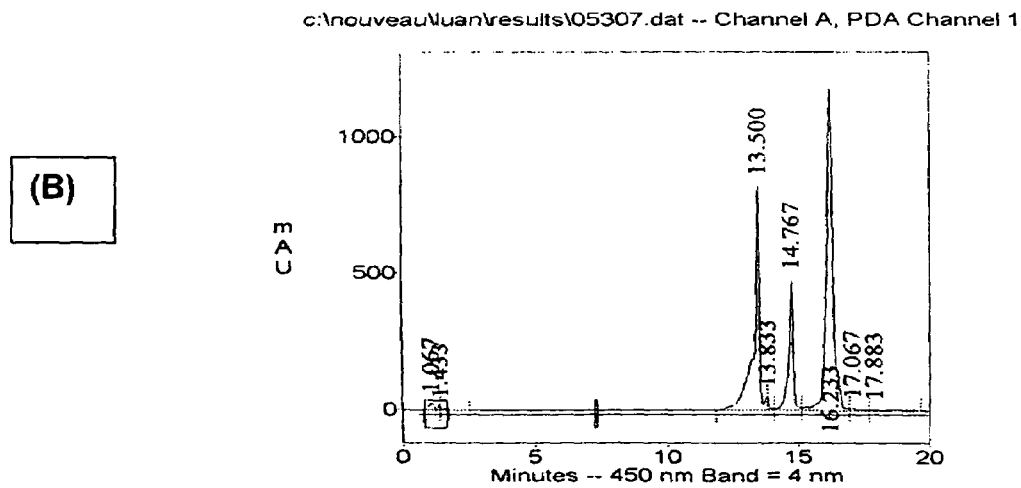

FIG. 3A is a plasmid map of pCRT24. FIG. 3B shows HPLC results confirming the presence of zeaxanthin in Methylomonas cells transformed with pCRT24.

The invention can be more fully understood from the following detailed description and the accompanying sequence descriptions, which form a part of this application.

The following sequences conform with 37 C.F.R. 1.821–1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. § 1.822.

SEQ ID NOs:1–18 are full length coding regions (open reading frames, or ORFs), proteins, or promoter fragments, as identified in Table 1.

TABLE 1

Summary of DNA and Protein SEQ ID Numbers

| Description | SEQ ID Nucleic acid | SEQ ID Peptide | SEQ ID Nucleic acid (Promoter Fragment) |
|---|---|---|---|
| Nitrogen transporter (nrtA) | 1 | 2 | 3 |
| Nitrogen regulating PII-protein (glnB) | 4 | 5 | 6 |
| Glyoxalase ii (glyoxII) | 7 | 8 | 9 |
| Heat shock protein (htpG) | 10 | 11 | 12 |
| Methanol dehydrogenase (moxF) | 13 | 14 | 15 |
| Hexulose-6-phosphate syntase (hps) | 16 | 17 | 18 |

SEQ ID NOs:19 and 20 are primers used for amplification of the moxF promoter.

SEQ ID NOs:21 and 22 are primers used for amplification of the hps promoter.

SEQ ID NOs:23–26 are primers used for deletion of the crtX coding region.

Applicants made the following biological deposits under the terms of the Budapest Treaty on the International Recognition of the Deposit of Microorganisms for the Purposes of Patent Procedure:

| Depositor Identification Reference | International Depository Designation | Date of Deposit |
|---|---|---|
| Methylomonas 16a | ATCC PTA 2402 | Aug. 22, 2000 |

DETAILED DESCRIPTION OF THE INVENTION

The present invention describes the isolation and characterization of inducible genes and their promoters from a high growth methanotrophic bacterial strain, Methylomonas sp. 16a. These promoters that are responsive to growth on methane and methanol and induction by the presence of nitrate, a change in growth temperature, or modification of media pH, will be useful to regulate the production of biomass including proteins, carbohydrates and pigments in Methylomonas sp. 16a and other C1 metabolizing bacteria. Thus, the present invention advances the art by providing:

(i) A method for the expression of a coding region of interest in a C1 metabolizing bacteria by nitrate induction;

(ii) A method for the expression of a coding region of interest in a C1 metabolizing bacteria by low pH (~5.5) induction;

(iii) A method for the expression of a coding region of interest in a C1 metabolizing bacteria by elevating growth temperature as an inducing condition; and (iv) A method for the expression of a coding region of interest in a C1 metabolizing bacteria by growth in methane or methanol.

In addition, nucleic acid sequences homologous to the present coding regions, or ORFs, and promoter fragments of the invention are expected to function in a similar manner for related applications in other C1 metabolizing bacteria.

Definitions

In this disclosure, a number of terms and abbreviations are used.

The following definitions are provided.

"Open reading frame" is abbreviated ORF.

"Polymerase chain reaction" is abbreviated PCR.

The term "genomic DNA" refers to the total DNA from an organism.

The term "total RNA" refers to the non-fractionated RNA from an organism.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to RNA that is without introns and that can be translated into protein by the cell. "cDNA" refers to a double-stranded DNA that is complementary to and derived from mRNA. "Sense" RNA refers to a RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 9928508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

The term "expression", as used herein, refers to the transcription and stable accumulation of sense (mRNA) or antisense RNA derived from a coding sequence. Expression may also refer to translation of mRNA into a polypeptide.

The term "up-regulated" as applied to gene expression means the mRNA transcriptional level of a particular gene or region in the test condition is increased relative to the control condition. In contrast, the term "down-regulated" as applied to gene expression means the mRNA transcriptional level of a particular gene or region in the test condition is decreased relative to the control condition.

The term "growth cycle" as applied to a cell refers to the metabolic cycle through which a cell moves in culture conditions. The cycle may be divided into various stages known as the exponential phase, the end of exponential phase, and the stationary phase.

The term "exponential growth", "exponential phase growth", "log phase" or "log phase growth" refer to the rate at which microorganisms are growing and dividing. When growing in log phase microorganisms are growing at the maximal rate possible given their genetic potential, the nature of the medium, and the conditions under which they are grown. Microorganism rate of growth is constant during exponential phase and the microorganism divides and doubles in number at regular intervals. Cells that are "actively growing" are those that are growing in log phase. In contrast to the definition of "exponential growth", the term "stationary phase" refers to the growth cycle phase where cell growth in a culture slows or even ceases. The term "growth-altering environment" refers to energy, chemicals, or living things that have the capacity to either inhibit cell growth or kill cells. Inhibitory agents may include, but are not limited to: mutagens, antibiotics, UV light, gamma-rays, x-rays, extreme temperature, phage, macrophages, organic chemicals and inorganic chemicals.

"State of the cell" refers to metabolic state of the organism when grown under different conditions.

The term "expression profile" refers to the expression of groups of genes under a given set of conditions.

The term "gene expression profile" refers to the expression of an individual gene and of suites of individual genes.

The term "DNA microarray" or "DNA chip" means the assembling of PCR products of a group of genes or all genes within a genome on a solid surface in a high density format or array. General methods for array construction and use are available (for example, see Schena M., et al. *Science.* 270(5235): 467–70 (1995). A DNA microarray allows for analysis of gene expression patterns or profiles of many genes to be performed simultaneously by hybridizing the DNA microarray comprising these genes or PCR products of these genes with cDNA probes prepared from the sample to be analyzed. DNA microarray or "chip" technology permits examination of gene expression on a genomic scale, allowing transcription levels of many genes to be measured simultaneously. Briefly, the technology comprises arraying microscopic amounts of DNA complementary to genes of interest or open reading frames on a solid surface at defined positions. This solid surface is generally a glass slide or a membrane (e.g., nylon). The DNA sequences may be arrayed by spotting or by photolithography. Two separate fluorescently-labeled probe mixes prepared from the two sample(s) to be compared are hybridized to the microarray. The presence and amount of the bound probes are detected by fluorescence, following laser excitation using a scanning confocal microscope, and quantitated using a laser scanner and appropriate array analysis software packages. Cy3 (green) and Cy5 (red) fluorescent labels are routinely used in the art; however, other similar fluorescent labels may also be employed. To obtain and quantitate a gene expression profile or pattern between the two compared samples, the ratio between the signals in the two channels (red:green) is calculated with the relative intensity of Cy5/Cy3 probes taken as a reliable measure of the relative abundance of specific mRNAs in each sample. Materials for the construction of DNA microarrays are commercially available: Affymetrix (Santa Clara, Calif.); Sigma Chemical Company (St. Louis, Mo.); Genosys (The Woodlands, Tex.); Clontech (Palo Alto, Calif.); and Corning (Corning, N.Y.). In addition, custom-made DNA microarrays can be prepared by commercial vendors such as Affymetrix, Clontech, and Corning.

The term "C1 carbon substrate" refers to any carbon-containing molecule that lacks a carbon-carbon bond. Examples are methane, methanol, formaldehyde, formic acid, formate, methylated amines (e.g., mono-, di-, and tri-methyl amine), methylated thiols, and carbon dioxide.

The term "C1 metabolizer" refers to a microorganism that has the ability to use a single carbon substrate as its sole source of energy and biomass. C1 metabolizers will typically be methylotrophs and/or methanotrophs.

The term "C1 metabolizing bacteria" refers to bacteria that have the ability to use a single carbon substrate as their sole source of energy and biomass. C1 metabolizing bacteria, a subset of C1 metabolizers, will typically be methylotrophs and/or methanotrophs.

The term "methylotroph" means an organism capable of oxidizing organic compounds that do not contain carbon-carbon bonds. Where the methylotroph is able to oxidize $CH_4$, the methylotroph is also a methanotroph.

The term "methanotroph" or "methanotrophic bacteria" means a prokaryote capable of utilizing methane as its primary source of carbon and energy. Complete oxidation of methane to carbon dioxide occurs by aerobic degradation pathways. Typical examples of methanotrophs useful in the present invention include but are not limited to the genera *Methylomonas, Methylobacter, Methylococcus*, and *Methylosinus*.

The term "high growth methanotrophic bacterial strain" refers to a bacterium capable of growth with methane or methanol as the sole carbon and energy source and which possesses a functional Embden-Meyerof carbon flux pathway, resulting in a high rate of growth and yield of cell mass per gram of C1 substrate metabolized (see WO 02/20728). The specific "high growth methanotrophic bacterial strain" described herein is referred to as "*Methylomonas* 16a", "16a" or "*Methylomonas* sp. 16a", which terms are used interchangeably and which refer to the *Methylomonas* strain used in the present invention.

A "nucleic acid" is a polymeric compound comprised of covalently linked subunits called nucleotides. Nucleic acids include polyribonucleic acid (RNA) and polydeoxyribonucleic acid (DNA), both of which may be single-stranded or double-stranded. DNA includes cDNA, genomic DNA, synthetic DNA, and semi-synthetic DNA.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid fragment is "hybridizable" to another nucleic acid fragment, such as a cDNA, genomic DNA, or RNA, when a single stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Ed., Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms) to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washed with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementarity, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as the length of the probe.

The term "oligonucleotide" refers to a nucleic acid, generally of at least 18 nucleotides, that is hybridizable to a genomic DNA molecule, a cDNA molecule, or an mRNA molecule. Oligonucleotides can be labeled, e.g., with $^{32}$P-nucleotides or nucleotides to which a label, such as biotin, has been covalently conjugated. In one embodiment, a labeled oligonucleotide can be used as a "probe" to detect the presence of a nucleic acid according to the invention. Thus, the term "probe" refers to a single-stranded nucleic acid molecule that can base pair with a complementary single stranded target nucleic acid to form a double-stranded molecule. The term "label" will refer to any conventional molecule which can be readily attached to mRNA or DNA and which can produce a detectable signal, the intensity of which indicates the relative amount of hybridization of the labeled probe to the DNA fragment. Preferred labels are fluorescent molecules or radioactive molecules. A variety of well-known labels can be used.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., J. Mol. Biol. 215:403–410 (1993). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular microbial proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing, as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including (but not limited to) those described in: Computational Molecular Biology (Lesk, A. M., ed.) Oxford University Press, NY (1988); Biocomputing: Informatics and Genome Projects (Smith, D. W., ed.) Academic Press, NY (1993); Computer Analysis of Sequence Data, Part I (Griffin, A. M., and Griffin, H. G., eds.) Humana Press, NJ (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

"Codon degeneracy" refers to the nature in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the instant microbial polypeptides as set forth in SEQ ID NOs:2, 5, 8, 11, 14, 17, and 20. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. Chimeric genes of the present invention will typically comprise an inducible promoter operably linked to a coding region of interest. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The term "inducible gene" means any gene with high expression in response to a specific stress, stimulus, or growth condition. Inducible genes of the present invention include the genes identified as nrtA, glnB, glyoxII, htpg, moxF, and hps of *Methlomonas* sp. 16a.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

The term "homolog", as applied to a gene, means any gene derived from the same or a different microbe having the same function. A homologous gene may have significant sequence similarity.

"Coding sequence" or "coding region of interest" refers to a DNA sequence that codes for a specific amino acid sequence.

"Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures.

"Transcriptional and translational control sequences" are DNA regulatory sequences, such as promoters, enhancers, terminators, and the like, that provide for the expression of a coding sequence in a host cell. In eukaryotic cells, polyadenylation signals are control sequences.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity. "Inducible promoter" means any promoter that is responsive to a particular stimulus. Inducible promoters of the present invention will typically be derived from the "inducible genes" and will be responsive to various metabolic conditions (growth substrate, nutrient composition, or environmental stress such as pH and temperature changes).

The terms "subfragment that is functionally equivalent" and "functionally equivalent subfragment" are used interchangeably herein. These terms refer to a portion or subsequence of an isolated nucleic acid fragment that retains the ability to confer gene expression or produce a certain phenotype. For example, the fragment or subfragment can be used for the expression of chimeric genes to produce the desired phenotype in a transformed host. The subfragment retains the promoter activity of the original full nucleic acid promoter fragment.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

"Mature" protein refers to a post-translationally processed polypeptide (i.e., any pre- or propeptides present in the primary translation product have been removed). "Precursor" protein refers to the primary product of translation of mRNA (i.e., with pre- and propeptides still present). Pre- and propeptides may be but are not limited to intracellular localization signals.

The term "signal peptide" refers to an amino terminal polypeptide preceding a secreted mature protein. The signal peptide is cleaved from, and is therefore not present in, the mature protein. Signal peptides have the function of directing and translocating secreted proteins across cell membranes. A signal peptide is also referred to as a signal protein.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid" and "vector" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation vector" refers to a specific plasmid containing a foreign gene and having elements in addition to the foreign gene that facilitate transformation of a particular host cell. "Expression cassette" refers to a DNA fragment containing a coding region and having elements in addition to the coding region that allow for expression of that coding region in a specific host.

The term "altered biological activity" will refer to an activity, associated with a protein encoded by a microbial nucleotide sequence, which can be measured by an assay method—where that activity is either greater than or less than the activity associated with the native microbial sequence. "Enhanced biological activity" refers to an altered activity that is greater than that associated with the native sequence. "Diminished biological activity" is an altered activity that is less than that associated with the native sequence.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: the GCG suite of programs (Wisconsin Package Version 9.0, Genetics Computer Group (GCG), Madison, Wis.); BLASTP, BLASTN, BLASTX (Altschul et al., *J. Mol. Biol.* 215:403–410 (1990); DNASTAR (DNASTAR, Inc., Madison, Wis.); and the FASTA program incorporating the Smith-Waterman algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.). Within the context of this application it will be understood that where sequence analysis software is used for analysis, the results of the analysis are based on the "default values" of the program referenced, unless otherwise specified. As used herein "default values" will mean any set of values or parameters which originally load with the software when first initialized.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Press, Cold Spring Harbor, N.Y. (1984); and by Ausubel, F. M. et al., *Current Protocols in Molecular Biology*, published by Greene Publishing Assoc. and Wiley-Interscience (1987).

Identification of Natural *Methylomonas* sp. 16a Promoters

The present invention identifies a number of inducible genes contained within the *Methylomonas* genome that are responsive to various metabolic conditions. These genes are regulated in response to nitrate, pH, temperature, or growth in methane or methanol. More specifically, promoter regions that regulate nrtA, glnB, glyoxII, htpg, moxF and hps have been identified as useful for driving expression of any suitable coding region of interest in C1 metabolizing bacteria.

Application of Microarrays

Investigation of promoter activity in *Methylomonas* or any other bacterium often employs Northern blots, enzymatic assays, and reporter genes. These methods permit monitoring of the effect of environmental changes on gene expression by comparing expression levels of a limited number of genes. Although they often enable investigation of one or a subset of the physiological conditions, these methods typically fail to monitor the comprehensive responses of a preponderance of individual genes in the genome of an organism in a reliable and useful manner.

With the advances in genomic research, a powerful new way to identify promoters is the use of DNA microarrays. DNA microarray technology is used to explore gene expression profiles on a genome-wide scale (DeRisi, J. L., et al., *Science* 278: 680–686 (1997)). It allows for the identification of genes that are expressed in different growth stages or environmental conditions. Promoters isolated from the identified genes can then be used to express other coding regions in the growth stage or under the environmental conditions characteristic of the promoter. The gene sequences themselves may be used as probes to follow gene expression activity, which is valuable for industrial environments where the conditions for promoter induction must be convenient, cost effective and compatible with a specific bio-manufacturing process. Thus the identified gene sequences may be used to analyze the state of the biomass and cell response to growth conditions in a bioreactor.

Generation of Microarrays

The invention identifies a number of *Methylomonas* sp. 16a genes as being responsive to various conditions not heretofore appreciated. The identification of these genes as being regulated by the new inducing conditions was made by means of the application of DNA microarray technology to the *Methylomonas* sp. 16a genome. Any C1 metabolizing bacterial species may be used, however *Methylomonas* sp. strain 16a is preferred.

The generation of DNA microarrays is common and well known in the art (e.g., Brown et al., U.S. Pat. No. 6,110,426). Typically, the generation of a microarray begins by providing a nucleic acid sample representing the genome of the organism of interest. Typically, the ORFs of this nucleic acid sample are amplified to produce DNA fragments of the same sequence by methods of primer directed amplification such as, for example: polymerase chain reaction (PCR) (U.S. Pat. No. 4,683,202 (1987, Mullis, et al.) and U.S. Pat. No. 4,683,195 (1986, Mullis, et al.); ligase chain reaction (LCR) (Tabor et al., *Proc. Acad. Sci. U.S.A.,* 82:1074–1078 (1985)); and/or, strand displacement amplification (Walker et al., *Proc. Natl. Acad. Sci. U.S.A.,* 89: 392 (1992)). The denatured, amplified ORF DNA fragments are then spotted on slides comprised of glass or some other solid substrate by methods well known in the art to form a micro-array. Methods of forming high-density arrays of oligonucleotides, with a minimal number of synthetic steps are known (see for example Brown et al., U.S. Pat. No. 6,110,426). The oligonucleotide analogue array can be synthesized on a solid substrate by a variety of methods, including, but not limited to: light-directed chemical coupling and mechanically directed coupling. See Pirrung et al., U.S. Pat. No. 5,143,854 (also PCT Application No. WO 90/15070) and Fodor et al., PCT Publication NOs. WO 92/10092 and WO 93/09668, which disclose methods of forming vast arrays of peptides, oligonucleotides and other molecules using, for example, light-directed synthesis techniques. See also, Fodor et al., *Science,* 251:767–77 (1991).

The ORF DNA fragments are arrayed in high density on at least one glass microscope slide. Once all the ORFs from the genome are amplified, and the amplified DNA fragments are isolated and arrayed, a set of probes, bearing a signal generating label are synthesized. Typically probes are generated from mRNA transcript(s) of the gene(s), or nucleic acids derived from the mRNA transcript(s), of the organism of interest. As used herein, a nucleic acid derived from an mRNA transcript refers to the nucleic acid produced from a particular mRNA transcript or a sub-sequence thereof (i.e., the mRNA transcript serves as a template for the nucleic acid so derived). Thus, a cDNA reverse transcribed from an mRNA, an RNA transcribed from that cDNA, a DNA amplified from the cDNA, an RNA transcribed from the amplified DNA, etc., are all derived from the mRNA transcript and detection using such derived products is indicative of the presence and/or abundance of the original transcript in a sample. Thus, suitable samples include, but are not limited to: mRNA transcripts of the gene(s), cDNA reverse transcribed from the mRNA, cRNA transcribed from the cDNA, DNA amplified from the gene(s), RNA transcribed from amplified DNA, and the like. Probes may be randomly generated or may be synthesized based on the sequence of specific open reading frames. Probes are typically single stranded nucleic acid sequences that are complementary to the nucleic acid sequences to be detected. Probes are "hybridizable" to the ORF DNA fragments of the array. The probe length can vary from 5 bases to tens of thousands of bases, and will depend upon the specific test to be done. Typically, a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Signal-generating labels that may be incorporated into the probes are well known in the art. For example, labels may include (but are not limited to): fluorescent moieties, chemiluminescent moieties, particles, enzymes, radioactive tags, or light emitting moieties or molecules. Fluorescent moieties are preferred. Most preferred are fluorescent dyes capable of attaching to nucleic acids and emitting a fluorescent signal. A variety of dyes are known in the art such as fluorescein, Texas Red, and rhodamine. Preferred are the mono reactive dyes Cy3 and Cy5, both available commercially (i.e. Amersham Pharmacia Biotech, Arlington Heights, Ill.). Suitable dyes are discussed in U.S. Pat. No. 5,814,454, hereby incorporated by reference.

Labels may be incorporated by any of a number of means well known to those of skill in the art. However, in a preferred embodiment, the label is simultaneously incorporated during the amplification step in the preparation of the probe nucleic acids. Thus, for example, polymerase chain reaction (PCR) with labeled primers or labeled nucleotides will provide a labeled amplification product. In a preferred embodiment, reverse transcription or replication using a labeled nucleotide (e.g. dye-labeled UTP and/or CTP) incorporates a label into the transcribed nucleic acids.

Alternatively, a label may be added directly to the original nucleic acid sample (e.g., mRNA, polyA mRNA, cDNA, etc.) or to the amplification product after the synthesis is completed. Means of attaching labels to nucleic acids are well known to those of skill in the art and include, for example, nick translation or end-labeling (e.g. with a labeled RNA) by treatment of the nucleic acid with kinase and subsequent attachment (ligation) of a nucleic acid linker joining the sample nucleic acid to the label (e.g., a fluorophore).

Following incorporation of the label into the probe the probes are then hybridized to the micro-array using standard conditions where hybridization results in a double stranded nucleic acid, one strand being a nucleic acid spotted on the array and one strand being a probe, generating a detectable signal from the label at the site of hybridization of the probe on the array. Typically, the probe and array must be mixed with each other under conditions that permit nucleic acid hybridization. This involves contacting the probe and array in the presence of an inorganic or organic salt under the proper concentration and temperature conditions. The probe and array nucleic acids must be in contact for a long enough time that any possible hybridization between the probe and sample nucleic acid may occur. The concentration of probe or array in the mixture will determine the time necessary for hybridization to occur. The higher the probe or array concentration the shorter the hybridization incubation time needed. Optionally a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen. *Nucl.*

*Acids Res.* 19:5143–5151(1991)). Suitable chaotropic agents include: guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3 M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1 M sodium chloride, about 0.05 to 0.1 M buffers, such as sodium citrate, Tris-HCl, PIPES or HEPES (pH range about 6–9), about 0.05 to 0.2% detergent, such as sodium dodecylsulfate, or between 0.5–20 mM EDTA, FICOLL (Pharmacia Inc.) (about 300–500 kilodaltons), polyvinylpyrrolidone (about 250–500 kdal), and serum albumin. Also included in the typical hybridization solution will be unlabeled carrier nucleic acids from about 0.1 to 5 mg/mL (fragmented nucleic DNA, e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate), and anionic saccharidic polymers (e.g., dextran sulfate). Methods of optimizing hybridization conditions are well known to those of skill in the art (see, for example, Laboratory Techniques in Biochemistry and Molecular Biology, Vol. 24: Hybridization With Nucleic Acid Probes, P. Tijssen, ed. Elsevier, N.Y., (1993); and Maniatis, supra).

Identification of Inducible Genes

The basis of gene expression profiling via microarray technology relies on comparing mRNAs present in an organism under a variety of conditions that result in alterations of the gene expression patterns. Within the context of the present invention separate populations of cells were exposed to different stresses that resulted in the alteration of gene expression patterns. The stresses or inducing conditions analyzed included: 1) nitrate; 2) low pH (~5.5); 3) elevated temperature (about 41–42° C.)--); and 4) growth in methane or methanol. Non-stressed cells were used for generation of "control" array data and stressed cells were used to generate "experimental", "stressed" or "induced" array data.

Using the above described method of DNA microarray technology and comparing gene expression patterns in induced versus non-induced cultures of *Methylomonas* sp. 16a, using a variety of different inducing conditions, it was determined that:

(a) the genes nrtA and glnB are induced by growth in the presence of nitrate;
(b) the glyoxll gene is induced by growth in the presence of low pH (~5.5);
(c) the htpG gene is induced by growth at elevated temperatures (e.g., 42° C. in the mesophilic *Methylomonas* sp. 16a); and
(d) the genes hps and moxF are constitutively expressed when grown in the presence of methanol and/or methane.

Comparison of the amino acid sequence encoded by the *Methylomonas* sp. 16a nitrogen transporter nrtA coding region sequence to public databases reveals that the most similar known sequence is 34% identical to the amino acid sequence of nrtA reported herein over the length of 464 amino acids using a Smith-Waterman alignment algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.). Preferred nucleic acid fragments of the invention encode a polypeptide of at least about 60%–70% identity to the amino acid sequence herein, where about 70%–90% is more preferred. Most preferred are nucleic acid fragments that encode a polypeptide of at least 95% identity to the amino acid sequence reported herein. Similarly, preferred nrtA encoding nucleic acid sequences corresponding to the instant ORF are those encoding functional proteins, and which are at least 80% identical to the nucleic acid sequence of nrtA reported herein. More preferred nrtA nucleic acid fragments are at least 90% identical to the sequence herein. Most preferred are nrtA nucleic acid fragments that are at least 95% identical to the nucleic acid sequence reported herein.

Comparison of the amino acid sequence encoded by the *Methylomonas* sp. 16a nitrogen regulator protein glnB coding region sequence to public databases reveals that the most similar known sequence is 76% identical to the amino acid sequence of glnB reported herein over the length of 112 amino acids using a Smith-Waterman alignment algorithm (W. R. Pearson supra). Preferred nucleic acid fragments of the invention encode a polypeptide of at least about 78%–90% identity to the sequence herein, where about 80%–90% is more preferred. Most preferred are nucleic acid fragments that encode a polypeptide of at least 95% identity to the amino acid sequence reported herein. Similarly, preferred glnB encoding nucleic acid sequences corresponding to the instant ORF are those encoding functional proteins, and which are at least 80% identical to the nucleic acid sequence of glnB reported herein. More preferred glnB nucleic acid fragments are at least 90% identical to the sequence herein. Most preferred are glnB nucleic acid fragments that are at least 95% identical to the nucleic acid sequence reported herein.

Comparison of the amino acid sequence encoded by the *Methylomonas* sp. 16a putative glyoxalase II glyoxll coding region sequence to public databases reveals that the most similar known sequence is 51% identical to the amino acid sequence of glyoxll reported herein over the length of 231 amino acids using a Smith-Waterman alignment algorithm (W. R. Pearson, supra). Preferred nucleic acid fragments of the invention encode a polypeptide of at least about 70%–80% identity to the sequence herein, where about 80%–90% is more preferred. Most preferred are nucleic acid fragments that encode a polypeptide of at least 95% identity to the amino acid sequence reported herein. Similarly, preferred glyoxll encoding nucleic acid sequences corresponding to the instant ORF are those encoding functional proteins, and which are at least 80% identical to the nucleic acid sequence of glyoxll reported herein. More preferred glyoxll nucleic acid fragments are at least 90% identical to the sequence herein. Most preferred are glyoxll nucleic acid fragments that are at least 95% identical to the nucleic acid sequence reported herein.

Comparison of the amino acid sequence encoded by the *Methylomonas* sp. 16a heat shock protein htpG coding region sequence to public databases reveals that the most similar known sequence is 57% identical to the amino acid sequence of htpG reported herein over the length of 644 amino acids using a Smith-Waterman alignment algorithm (W. R. Pearson, supra). Preferred nucleic acid fragments of the invention encode a polypeptide of at least about 70%–80% identity to the sequence herein, where about 80%–90% is more preferred. Most preferred are nucleic acid fragments that encode a polypeptide of at least 95% identity to the amino acid sequence reported herein. Similarly, preferred htpG encoding nucleic acid sequences corresponding to the instant ORF are those encoding functional proteins, and which are at least 80% identical to the nucleic acid sequence of htpG reported herein. More preferred htpG nucleic acid fragments are at least 90% identical to the sequence herein. Most preferred are htpG nucleic acid fragments that are at least 95% identical to the nucleic acid sequence reported herein.

Comparison of amino acid sequence encoded by the Methylomonas sp. 16a methanol dehydrogenase subunit moxF coding region sequence to public databases reveals that the most similar known sequence is 60% identical to the amino acid sequence of moxF reported herein over the length of 89 amino acids using a Smith-Waterman alignment algorithm (W. R. Pearson, supra). Preferred nucleic acid fragments of the invention encode a polypeptide of at least about 70%–80% identity to the sequence herein, where about 80%–90% is more preferred. Most preferred are nucleic acid fragments that encode a polypeptide of at least 95% identity to the amino acid sequence reported herein. Similarly, preferred moxF encoding nucleic acid sequences corresponding to the instant ORF are those encoding functional proteins, and which are at least 80% identical to the nucleic acid sequence of moxF reported herein. More preferred moxF nucleic acid fragments are at least 90% identical to the sequence herein. Most preferred are moxF nucleic acid fragments that are at least 95% identical to the nucleic acid sequence reported herein.

Comparison of the amino acid sequence encoded by the Methylomonas sp. 16a hexulose-6-phosphate synthase (hps) coding region sequence to public databases reveals that the most similar known sequence is 55% identical to the amino acid sequence of hps reported herein over the length of 215 amino acids using a Smith-Waterman alignment algorithm (W. R. Pearson, supra). Preferred nucleic acid fragments of the invention encode a polypeptide of at least about 70%–80% identity to the sequence herein, where about 80%–90% is more preferred. Most preferred are nucleic acid fragments that encode a polypeptide of at least 95% identity to the amino acid sequence reported herein. Similarly, preferred hps encoding nucleic acid sequences corresponding to the instant ORF are those encoding functional proteins, and which are at least 80% identical to the nucleic acid sequence of hps reported herein. More preferred hps nucleic acid fragments are at least 90% identical to the sequence herein. Most preferred are hps nucleic acid fragments that are at least 95% identical to the nucleic acid sequence reported herein.

Isolation of Homologs to the Inducible Genes

It will be appreciated by a person of skill in the art that the genes of the present invention have homologs in a variety of C1 metabolizing bacterial species; and, the use of the gene promoters for heterologous gene expression and the gene or ORF nucleic acid sequences for monitoring of bioreactor health and production are not limited to those genes derived from Methylomonas sp. 16a, but extend to homologs in any C1 metabolizing bacterial species. For example, the invention encompasses homologs derived from species including, but not limited to: Methylomonas, Methylobacter, Methylococcus, Methylosinus, Methylocyctis, Methylomicrobium, Methanomonas, Methylophilus, Methylobacillus, Methylobacterium, Hyphomicrobium, Xanthobacter, Bacillus, Paracoccus, Nocardia, Arthrobacter, Rhodopseudomonas, and Pseudomonas.

As is well known in the art, isolation of homologous genes using sequence-dependent protocols is readily possible using various techniques. Examples of sequence-dependent protocols include, but are not limited to: 1.) methods of nucleic acid hybridization; and 2.) methods of DNA and RNA amplification (described previously). For example, genes encoding similar proteins or polypetides to those of the instant invention could be isolated directly by using all or a portion of the instant nucleic acid fragments as DNA hybridization probes to screen libraries from any desired bacteria using methodology well known to those skilled in the art. Specific oligonucleotide probes based upon the instant nucleic acid sequences can be designed and synthesized by methods known in the art (Maniatis, supra). Moreover, nucleic acvid sequences of the invention can be used directly to synthesize DNA probes by methods known to the skilled artisan such as random primers DNA labeling, nick translation, or end-labeling techniques; or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotide as specific hybridization probes in the Diagnosis of Genetic Disorders", in Human Genetic Diseases: A Practical Approach, K. E. Davis Ed., (1986) pp 33–50 IRL Press, Herndon, Va.); Rychlik, W. (1993) In White, B. A. (ed.), Methods in Molecular Biology, Vol. 15, pp 31–39, PCR Protocols: Current Methods and Applications; Humania Press, Inc., Totowa, N.J.).

Generally two short segments of the instant sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., PNAS USA 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (Gibco/BRL), specific 3' or 5' cDNA fragments can be isolated (Ohara et al., PNAS USA 86:5673 (1989); Loh et al., Science 243:217 (1989)).

Optionally, the instant sequences may be employed as hybridization reagents for the identification of homologs. The basic components of a nucleic acid hybridization test include a probe, a sample suspected of containing the gene or gene fragment of interest, and a specific hybridization method. Techniques are similar to those employed for microarray hybridization.

Identification of Promoter Regions Based on Microarray Data

Promoter regions are generally located 5' to the coding region in a gene. Promoter regions in bacterial genomes exist for coding regions that are the 5' most ORF in an operon composed of multiple ORFs. Thus the location in the genome of a coding region is analyzed to determine whether a promoter region lies 5' to that specific coding region. Specifically, the DNA sequence surrounding the coding region (both 5' and 3') is examined for the presence of additional ORFs. In general, when there is no ORF found 5' and adjacent to an ORF of interest, or the next 5' ORF is in the opposite orientation, then the ORF of interest has a promoter 5' and adjacent to it. If there are additional ORFs in the same orientation and 3' adjacent to the ORF of interest, then the ORF of interest is the 5' most ORF of an operon. The upstream region to such an ORF of interest can be used as a promoter region. Typically, DNA regions containing about 100 bp downstream and 400 to 500 bp upstream from the ATG translational start site for the 5'-most coding region in an operon are used to ensure full promoter activity. Smaller fragments that do not extend as far to either 5' or 3' of the ATG translational start site may have full functional promoter activity. Thus subfragments of the promoter sequences of the invention, which are functionally equivalent subfragments that retain promoter activity, are also useful for expressing chimeric genes in *Methylomonas* and are one aspect of the invention herein.

Chimeric Gene Expression in C1 Metabolizing Bacteria

The promoter regions derived from the inducible genes identified herein (SEQ ID NOs:3, 6, 9, 12, 15, and 18) may be utilized in the construction of chimeric genes to be expressed in native host cells and heterologous host cells, particularly in the cells of C1 metabolizing bacterial hosts. The chimeric genes described herein comprise a promoter selected from one of the promoters of the invention, and a coding region of choice. Expression of chimeric genes in recombinant C1 metabolizing bacterial hosts may be useful for altering the composition of the bacterial cells. The chimeric genes are used in creating recombinant bacterial hosts using microbial transformation systems and vectors that are well known to those skilled in the art. Plasmids that can replicate in *E. coli* but not in *Methylomonas*, and can be transferred into *Methylomonas* can be used as vectors for integration. Using an integration vector, expression of the chimeric gene follows its integration into the bacterial genome. Alternatively, a promoter of the invention may be operably linked to a coding region of choice and cloned into a plasmid that is capable of replicating itself in a C1 metabolizing bacterium. Broad host range plasmids that are able to replicate in a variety of bacteria can be used in *Methylomonas* as well. The plasmid is transferred into a C1 metabolizing bacterium by conjugation using a helper bacterial strain.

Once the recombinant C1 metabolizing bacteria is established, expression of the chimeric gene can be accomplished by applying inducing conditions appropriate to the promoter used (e.g., growth on methane or methanol, nitrate addition, and/or modification of temperature or pH). One skilled in the art will readily be able to determine appropriate conditions of induction. For example, the htpG promoter (SEQ ID NO:12 for example) will likely be induced in mesophilic C1 metabolizing bacteria (those bacteria whose optimum growth temperature lies within a range generally accepted as about 20–45° C.) between the temperature range of about 41–42° C. In contrast, thermophilic bacteria (having an optimum growth temperature greater than about 45° C.) would likely require an inducing temperature of about 47–50° C. Similarly a C1 metabolizer transformed with a chimeric gene comprising a promoter region derived from the nrtA and glnB genes (SEQ ID NO:3 or SEQ ID NO:6 for example) would be expected to express this gene in the presence of nitrate. Typically levels of about 5 mM to about 15 mM will be suitable where levels of about 10 mM are preferred. In another aspect of the invention a C1 metabolizer having a chimeric gene comprising a promoter region derived from the glyoxll gene (SEQ ID NO:9 for example) will be expected to express the this gene at acidic pH's, for example at levels of about 5.5. Alternatively C1 metabolizer host cells having chimeric genes comprising promoter regions derived from the hps and moxF genes will be expected to express these genes when the cells are grown on or exposed to suitable levels of methanol and/or methane.

Vectors useful for the transformation of suitable C1 metabolizing bacterial host cells are well known in the art. Typically the vector contains a selectable marker, and sequences allowing autonomous replication or chromosomal integration. Chimeric genes to be introduced into a host cell may be cloned into the transformation vector. Chimeric genes comprise a region 5' of the coding region that harbors transcriptional initiation controls and a region 3' of the coding region that controls transcriptional termination. It is most preferred when both control regions are derived from genes homologous to the transformed host cell, although it is to be understood that such control regions need not be derived from the genes native to the specific species chosen as a production host.

Promoters which are useful to drive expression of the coding region of interest in the desired host cell are selected from those derived from the upstream portion of the nrtA, glnB, glyoxll, htpg, moxF and hps genes (SEQ ID NOs:1, 4, 7, 10, 13, and 16), as described in the instant invention as SEQ ID NOs:3, 6, 9, 12, 15, and 18. Choice of a particular promoter will depend on the method of regulation desired (induction in the presence of nitrate, temperature, or pH conditions; or by growth on methane or methanol). The promoter regions may be identified from the sequences of the inducible genes and their homologs (see Tables 5, 7, 9, and 11) and isolated according to common methods (Maniatis, supra). Once the promoter regions are identified and isolated, each may be operably linked to a coding region of interest in suitable transformation vectors.

Termination control regions may be derived from various genes native to the preferred hosts. Optionally, a termination site may be unnecessary; however, it is most preferred if included.

Preferred C1 Metabolizing Bacterial Hosts

Preferred heterologous host cells for expression of the instant genes and promoter fragments are C1 metabolizing bacteria that are able to use single carbon substrates as a sole energy source. Many C1 metabolizing microorganisms that are able to use a variety of single carbon substrates are known in the art. Single carbon substrates useful in the present invention include, but are not limited to: methane, methanol, formaldehyde, formic acid, methylated amines (e.g. mono-, di- and tri-methyl amine), methylated thiols, and carbon dioxide.

All C1 metabolizing microorganisms are generally classified as methylotrophs. Methylotrophs may be defined as any organisms capable of oxidizing organic compounds that do not contain carbon-carbon bonds. Facultative methylotrophs have the ability to oxidize organic compounds which do not contain carbon-carbon bonds, but may also use other carbon substrates such as sugars and complex carbohydrates for energy and biomass. Obligate methylotrophs are those organisms which are limited to the use of organic compounds that do not contain carbon-carbon bonds for the generation of energy. Finally, obligate methanotrophs (a subset of methylotrophs) are those obligate methylotrophs that have the distinctive ability to oxidize methane.

Facultative methylotrophic bacteria are found in many environments, but are isolated most commonly from soil, landfill and waste treatment sites. Many facultative methylotrophs are members of the β, and γ subgroups of the Proteobacteria (Hanson et al., *Microb. Growth C1 Compounds.*, [Int. Symp.], 7th (1993), 285–302. Editor(s): Murrell, J. Collin; Kelly, Don P. Publisher: Intercept, Andover, UK; Madigan et al., *Brock Biology of Microorganisms,* 8th edition, Prentice Hall, UpperSaddle River, N.J. (1997)). Facultative methylotrophic bacteria suitable in the present invention include, but are not limited to: *Methylophilus, Methylobacillus, Methylobacterium, Hyphomicrobium, Xanthobacter, Bacillus, Paracoccus, Nocardia, Arthrobacter, Rhodopseudomonas,* and Pseudomonas.

Those methylotrophs having the additional ability to utilize methane are referred to as methanotrophs. Of particular interest in the present invention are those obligate methanotrophs which are methane utilizers but which are obliged to use organic compounds lacking carbon-carbon bonds. Exemplary organisms included in this classification of obligate methanotrophs that utilize C1 compounds are the genera *Methylomonas, Methylobacter, Mehtylococcus, Methylosinus, Methylocyctis, Methylomicrobium,* and *Methanomonas,* although this is not intended to be limiting.

Of particular interest in the present invention are high growth obligate methanotrophs having an energetically favorable carbon flux pathway. For example, Applicants have discovered a specific strain of methanotroph having several pathway features that make it particularly useful for carbon flux manipulation (WO 02/20728). This particular strain possessing an energetically favorable carbon flux pathway served as the host organism from which SEQ ID NOs:1–18 were isolated and is known as *Methylomonas* 16a (ATCC PTA 2402).

Industrial Production

Where expression of a suitable coding region of interest is desired using an inducible promoter of the instant invention (selected from SEQ ID NOs:3, 6, 9, 12, 15, and 18) for commercial production of a product, a variety of culture methodologies may be applied. For example, large-scale production of a specific product made possible by chimeric gene expression in a recombinant microbial host may be accomplished by both batch and continuous culture methodologies.

A classical batch culturing method is a closed system where the composition of the media is set at the beginning of the culture and not subject to external alterations during the culturing process. Thus, at the beginning of the culturing process the media is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch culturing methods are common and well known in the art and examples may be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.,* 36:227 (1992), herein incorporated by reference.

Commercial production of a product of interest in a C1 metabolizing bacteria, using the methodology and promoters of the present invention, may also be accomplished with a continuous culture. Continuous cultures are open systems where a defined culture media is added continuously to a bioreactor and an equal amount of conditioned media is removed simultaneously for processing. Continuous cultures generally maintain the cells at a constant high liquid phase density where cells are primarily in log phase growth. Alternatively, continuous culture may be practiced with immobilized cells where carbon and nutrients are continuously added and valuable products, by-products, and waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems, a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes, as well as techniques for maximizing the rate of product formation, are well known in the art of industrial microbiology and a variety of methods are detailed by Brock, supra.

Regulated Expression of Suitable Coding Regions of Interest

The promoters of the present invention may be used to effect the regulated expression of chimeric genes in various C1 metabolizing bacteria under specific induction conditions. Useful chimeric genes will include the promoter region of any one of the inducible genes defined herein (SEQ ID NOs:1, 4, 7, 10, 13, and 16), operably linked to a suitable coding region of interest to be expressed in a C1 metabolizing bacterial host. These promoter regions are identified as SEQ ID NOs:3, 6, 9, 12, 15, and 18. Any host that is capable of accommodating the promoter region is suitable including, but not limited to: *Methylomonas, Methylobacter, Mehtylococcus, Methylosinus, Methylocyctis, Methylomicrobium, Methanomonas, Methylophilus, Methylobacillus, Methylobacterium, Hyphomicrobium, Xanthobacter, Bacillus, Paracoccus, Nocardia, Arthrobacter, Rhodopseudomonas,* and *Pseudomonas.*

Coding regions of interest to be expressed as a chimeric gene in a recombinant C1 metabolizing bacterial host may be either endogenous to the host or heterologous and must be compatible with the host organism. Sequences encoding proteins of commercial value are particularly suitable for expression. For example, suitable coding regions of interest may include, but are not limited to those encoding viral, bacterial, fungal, plant, insect, or vertebrate proteins of interest, including mammalian polypeptides. Further, these coding regions of interest may be, for example, structural proteins, enzymes, or peptides. A particularly preferred, but non-limiting list includes:

1) coding regions for enzymes involved in the central carbon pathway, such as transaldolase, fructose bisphosphate aldolase, keto deoxy phosphogluconate aldolase, phosphoglucomutase, glucose-6-phosphate isomerase, phosphofructokinase, 6-phosphogluconate dehydratase, 6-phosphogluconate-6-phosphate-1 dehydrogenase, and the like;

2) coding regions for enzymes involved in the production of isoprenoid molecules, such as 1-deoxyxylulose-5-phosphate synthase (dxs), 1-deoxyxylulose-5-phosphate reductoisomerase (dxr), geranyltransferase or farnesyl diphosphate synthase (ispA), 2C-methyl-D-erythritol cytidyltransferase (ispD), to 4-diphosphocytidyl-2-C-methylerythritol kinase (ispE), 2C-methyl-d-erythritol 2,4-cyclodiphosphate synthase (ispF), and geranylgeranyl pyrophosphate synthase (crtE);

3) coding regions for carotenoid pathway enzymes such as zeaxanthin glucosyl transferase (crtX), lycopene cyclase (crtY), phytoene dehydrogenase (crtZ), phytoene synthase (crtB), beta-carotene hydroxylase (crtZ), phytoene desaturase (crtD), beta-carotene ketolase (crtO, crtW), and the like, which would enable the production of carotenoids such as antheraxanthin, astaxanthin, canthaxanthin, α-carotene, β-carotene, ε-carotene, γ-carotene, ζ-carotene, alpha-cryptoxanthin, diatoxanthin, 7,8-didehydroastaxanthin, fucoxanthin, fucoxanthinol, lactucaxanthin, lutein, lycopene, neoxanthin, neurosporene, peridinin, phytoene, rhodopin, rhodopin glucoside, siphonaxanthin, spheroidene, spheroidenone, spirilloxanthin, uriolide, uriolide acetate, violaxanthin, and zeaxanthin;

4) coding regions for cyclic terpenoid synthases (e.g., limonene synthase) for the production of terpenoids, and the like;

5) coding regions for enzymes involved in the production of exopolysaccharides, such as UDP-glucose pyrophosphorylase (ugp), glycosyltransferase (gumD), polysaccharide export proteins (wza, espB), polysaccharide biosynthesis (espM), glycosyltransferase (waaE), sugar transferase (espV), galactosyltransferase (gumH), and glycosyltransferase genes and the like;

6) coding regions for enzymes involved in the production of aromatic amino acids, such as 3-deoxy-D-arabino-heptulosonate-7-phosphate synthase (aroG), 3-dehydroquinate synthase (aroB), 3-dehydroquinase or 3 dehydroquinate dehydratase (aroQ), 5-shikimic acid dehydrogenase (aroE), shikimic acid kinase (aroK), 5-enolpyruvylshikimate-3-phosphate synthase, chorismate synthase (aroC), anthranilate synthase (trpE), anthranilate phosphoribosyltransferase (trpD), indole 3-glycerol phosphate synthase (trpC), tryptophan synthetase (trpB), chorismate mutase or prephenate dehydratase (pheA), and prephenate dehydrogenase (tyrAc); and 7) coding regions of pds, phaC, phaE, efe, pdc, and adh genes and genes encoding pinene synthase, bornyl synthase, phellandrene synthase, cineole synthase, sabinene synthase, and taxadiene synthase.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory: Cold Spring Harbor, N.Y. (1989) (Maniatis) and by T. J. Silhavy, M. L. Bennan, and L. W. Enquist, Experiments with Gene Fusions, Cold Spring Harbor Laboratory: Cold Spring Harbor, N.Y. (1984) and by Ausubel, F. M. et al., Current Protocols in Molecular Biology, pub. by Greene Publishing Assoc. and Wiley-Interscience (1987).

The meaning of abbreviations is as follows: "hr" means hour(s), "min" means minute(s), "sec" means second(s), "d" means day(s), "mL" means milliliter(s), "μL" means microliter(s), "nL" means nanoliter(s), "ag" means microgram(s), "ng" means nanogram(s), "mM" means millimole(s), "μM" means micromole(s), "OD" means optical density.

Molecular Biology Techniques:

Methods for agarose gel electrophoresis were performed as described in Maniatis (supra). Polymerase Chain Reactions (PCR) techniques were found in White, B., *PCR Protocols: Current Methods and Applications*, Volume 15 (1993) Humana Press, Inc., Totowa, N.J.

Media and Culture Conditions:

General materials and methods suitable for the maintenance and growth of bacterial cultures are found in: *Experiments in Molecular Genetics* (Jeffrey H. Miller), Cold Spring Harbor Laboratory Press (1972); *Manual of Methods for General Bacteriology* (Phillip Gerhardt, R. G. E. Murray, Ralph N. Costilow, Eugene W. Nester, Willis A. Wood, Noel R. Krieg and G. Briggs Phillips, eds), pp. 210–213, American Society for Microbiology, Washington, D.C.; or, Thomas D. Brock in *Biotechnology: A Textbook of Industrial Microbiology*, Second Edition (1989) Sinauer Associates, Inc., Sunderland, Mass. All reagents and materials used for the growth and maintenance of bacterial cells were obtained from Aldrich Chemicals (Milwaukee, Wis.), DIFCO Laboratories (Detroit, Mich.), Gibco/BRL Life Technologies (Gaithersburg, Md.), or Sigma Chemical Company (St. Louis, Mo.) unless otherwise specified.

HPLC Analysis of Carotenoid Content

Cell pellets were extracted with 1 ml acetone by vortexing for 1 min and intermittent vortexing over the next 30 min.

Cell debris was removed by centrifugation at 14,000×g for 10 min and the supernatants was collected and passed through a 0.45 μM filter. A Beckman System Gold® HPLC with Beckman Gold Nouveau Software (Columbia, Md.) was used for the study. The crude extraction (0.1 mL) was loaded onto a 125×4 mm RP8 (5 μm particles) column with corresponding guard column (Hewlett-Packard, San Fernando, Calif.). The flow rate was 1 mL/min, while the solvent program used was: 0–11.5 min 40% water/60% methanol; 11.5–20 min 100% methanol; 20–30 min 40% water/60% methanol. The spectral data was collected by a Beckman photodiode array detector (model 168).

Example 1

Growth of Methylomonas 16a

Example 1 summarizes the standard conditions used for growth of *Methylomonas* sp. 16a (ATCC# PTA-2402), as described in WO02/20728.

Methylomonas Strain and Culture Media.

The growth conditions described below were used throughout the experimental Examples for treatment of *Methylomonas* 16a, unless conditions were specifically mentioned to be otherwise.

*Methylomonas* 16a was grown in serum stoppered Wheaton bottles (Wheaton Scientific, Wheaton, Ill.) using a gas/liquid ratio of at least 8:1 (i.e. 20 mL of Nitrate liquid "BTZ-3" medium in 160 mL total volume). The standard gas phase for cultivation contained 25% methane in air, although methane concentrations could vary ranging from about 5–50% by volume of the culture headspace. These conditions comprise growth conditions and the cells are referred to as growing cells. In all cases, the cultures were grown at 30° C. with constant shaking in a Lab-Line rotary shaker unless otherwise specified.

Nitrate medium for *Methylomonas* 16a

*Methylomonas* 16a was grown in a defined medium comprised of only minimal salts; no organic additions such as yeast extract or vitamins were required to achieve growth. This defined medium, also referred to herein as "nitrate liquid medium", or "BTZ-3" medium, was comprised of various salts mixed with Solution 1 as indicated below (Tables 2 and 3) or where specified the nitrate was replaced with 15 mM ammonium chloride. Solution 1 provides the composition for a 100 fold concentrated stock solution of trace minerals.

TABLE 2

Solution 1*

|  | MW | Conc. (mM) | g per L |
|---|---|---|---|
| Nitriloacetic acid | 191.1 | 66.9 | 12.8 |
| $CuCl_2 \times 2H_2O$ | 170.48 | 0.15 | 0.0254 |
| $FeCl_2 \times 4H_2O$ | 198.81 | 1.5 | 0.3 |
| $MnCl_2 \times 4H_2O$ | 197.91 | 0.5 | 0.1 |
| $CoCl_2 \times 6H_2O$ | 237.9 | 1.31 | 0.312 |
| $ZnCl_2$ | 136.29 | 0.73 | 0.1 |
| $H_3BO_3$ | 61.83 | 0.16 | 0.01 |
| $Na_2MoO_4 \times 2H_2O$ | 241.95 | 0.04 | 0.01 |
| $NiCl_2 \times 6H_2O$ | 237.7 | 0.77 | 0.184 |

*Mix the gram amounts designated above in 900 mL of $H_2O$, adjust to pH = 7, and add $H_2O$ to a final volume of 1 L. Keep refrigerated.

TABLE 3

Nitrate liquid medium (BTZ-3)**

|  | MW | Conc. (mM) | g per L |
|---|---|---|---|
| $NaNO_3$ | 84.99 | 10 | 0.85 |
| $KH_2PO_4$ | 136.09 | 3.67 | 0.5 |
| $Na_2SO_4$ | 142.04 | 3.52 | 0.5 |
| $MgCl_2 \times 6H_2O$ | 203.3 | 0.98 | 0.2 |
| $CaCl_2 \times 2H_2O$ | 147.02 | 0.68 | 0.1 |
| 1 M HEPES (pH 7) | 238.3 |  | 50 mL |
| Solution 1 |  |  | 10 mL |

**Dissolve in 900 mL $H_2O$. Adjust to pH = 7, and add $H_2O$ to give 1 L. For agar plates: Add 15 g of agarose in 1 L of medium, autoclave, let cool down to 50° C., mix, and pour plates.

Assessment of Microbial Growth and Conditions for Harvesting Cells

Cells grown to maximum optical density had an $OD_{660}$ of ~1.0. Cells were harvested by centrifugation in a Sorval RC-5B centrifuge using an SS-34 rotor at 6000 rpm for 20 min. The cell pellets were resuspended in 50 mM HEPES buffer, pH 7. These cell suspensions were referred to as washed, resting cells.

Microbial growth was assessed by measuring the optical density of the culture at 660 nm in an Ultrospec 2000 UV/Vis is spectrophotometer (Pharmacia Biotech, Cambridge, England) using a 1 cm light path cuvet. Alternatively, microbial growth was assessed by harvesting cells from the culture medium by centrifugation as described above and resuspending the cells in distilled water with a second centrifugation to remove medium salts. The washed cells were then dried at 105° C. overnight in a drying oven for dry weight determination.

Example 2

Construction of a DNA Microarray of the Methylomonas Genome

Example 2 describes the multi-step procedure required to create a DNA microarray of the *Methylomonas* genome. This array comprised 3750 ORFs, representing approximately 93% of the total genome of the organism. Also described are procedures for preparing probes, hybridizing probes to microarrays, and collecting the data generated.

Amplification of DNA Regions for the Construction of DNA Microarrays

Specific primer pairs were used in PCR reactions to amplify the DNA sequence of each protein encoding ORF of *Methylomonas* sp. 16a. Primers were designed based on the 5' and 3' sequences of each ORF by methods well known by one skilled in the art. Genomic DNA (10–30 ng) was used as the template. Genomic DNA was prepared using the Fast DNA Kit (Bio 101; Carlsbad, Calif.). The PCR reactions were performed in the presence of HotStart Taq™ DNA polymerase (Qiagen, Valencia, Calif.) and the dNTPs (Gibco/BRL). Thirty-five cycles of denaturation at 95° C. for 30 sec, annealing at 55° C. for 30 sec and polymerization at 72° C. for 2 min were conducted. PCR products were visualized following electrophresis on 1% argarose gels. The PCR amplified DNA samples were purified by the high-throughput PCR purification kit from Qiagen (Valencia, Calif.).

Arraying amplified ORFs

Before arraying, for each samp[le, an equal volume of DMSO (10 μL) and DNA (10 μL; about 50 ng/μL)sample was mixed in 384-well microtiter plates. A generation II DNA spotter (Molecular Dynamics, Sunnyvale, Calif.) was used to array the samples onto coated glass slides (Telechem, Sunnyvale, Calif.). Each PCR product was arrayed in duplicate on each slide. After cross-linking by UV light, the slides were stored under vacuum in a desiccator at room temperature until use.

RNA Isolation

Methylomonas 16a was cultured in nitrate liquid medium with ammonium or nitrate (10 mM) as the nitrogen source under 25% methane in air as described in Example 1. Samples of the culture (typically 20 mL) were harvested when the $OD_{660}$ reached 0.3 (exponential phase). Cell cultures were harvested quickly and ruptured in RLT buffer (Qiagen RNeasy Mini Kit, Valencia, Calif.) with a beads-beater (Bio101, Vista, Calif.). Debris was pelleted by centrifugation for 3 min at 14,000×g at 4° C. RNA isolation was completed using the protocol supplied with this kit. After on-column DNAase treatment, the RNA product was eluted with 50–100 μL RNAase-free distilled water. RNA preparations were stored frozen at either −20° C. or −80° C.

Synthesis of Fluorescent cDNA from Total RNA

RNA samples (7 to 15 μg) and random hexamer primers (6 μg; Gibco/BRL) were mixed and brought to a volume of 25 μL with RNAase-free water. Each sample was denatured at 70° C. for 10 min and then chilled on ice for 30 sec. After adding 14 μL of labeling mixture, annealing was accomplished by incubation at room temperature for 10 min. The labeling mixture contained 8 μL of 5× enzyme buffer, 4 μL DTT (0.1 M), and 2 μL of 20× dye mixture. The dye mixture consisted of 2 mM of each dATP, dGTP, and dTTP, 1 mM dCTP, and 1 mM of Cy3-dCTP or Cy5-dCTP. After adding 1 to 1.5 μL of SuperScript II reverse transcriptase (200 units/mL, Life Technologies Inc., Gaithersburg, Md.), cDNA synthesis was allowed to proceed at 42° C. for 2 hr. The RNA was removed by adding 2 μL NaOH (2.5 N) to the reaction. After 10 min of incubation at 37° C., the pH was adjusted with 10 μL of HEPES (2 M). The labeled cDNA was then purified with a PCR purification kit (Qiagen, Valencia, Calif.). Labeling efficiency was monitored using either $A_{550}$ for Cy3 incorporation, or $A_{650}$ for Cy5.

Fluorescent Labeling of Genomic DNA

Methylomonas sp. 16a genomic DNA, prepared as described above, was nebulized to approximately 2 kb pair fragments. The fragmented genomic DNA (0.5 to 1 μg) was mixed with 6 μg of random hexamers primers (Gibco/BRL) in 15 μL of water. The mix was denatured by placement in boiling water for 5 min. Then, the reaction was annealed on ice for 30 sec before being transferred to room temperature. Subsequently, 2 μL of 5× Buffer 2 (Gibco/BRL) and 2 ul dye mixture were added. The components of the dye mixture and the labeling procedure were the same as described above for RNA labeling, except that the Klenow fragment of DNA polymerase 1 (5 μg/μL, Gibco/BRL) was used as the enzyme. After incubation at 37° C. for 2 hr, the labeled DNA probe was purified using a PCR purification kit (Qiagen, Valencia, Calif.).

Hybridization and Washing

Slides were first incubated with prehybridization solution containing 3.5×SSC (Gibco/BRL), 0.1% SDS, 1% bovine serum albumin (BSA, Fraction V, Sigma) for 30 min at 37° C. After prehybridization, hybridization solutions (Molecular Dynamics, Sunnyvale, Calif.) containing 100 picomol of dye (Cy3 or Cy5) incorporated into the labeled probes, described in the Examples to follow, were added to the slides which were then covered with cover slips. Slides were placed in a humidified chamber in a 42° C. incubator. After overnight incubation, slides were initially washed for 5 min at room temperature with a solution containing 0.1×SSC and 0.1% SDS. Slides were then washed at 65° C. for 10 min with the same solution three times. After washing, the slides were rinsed quickly in distilled water and dried with a stream of nitrogen gas.

Data Collection and Analysis

The signal generated from each slide was quantified with a laser scanner (Molecular Dynamics, Sunnyvale, Calif.). The images were analyzed with ArrayVision 4.0 software (Imaging Research, Inc., Ontario, Canada). The raw fluorescent intensity for each spot was adjusted by subtracting the background. These readings were exported to spreadsheets for further analysis.

Example 3

Identification of Nitrate Induced DNA Regions in Methylomonas

Using a Methylomonas DNA microarray prepared according to the methods described in Example 2, Applicants identified two nitrate inducible genes. The promoters of these genes can be employed for directing chimeric gene expression in Methylomonas and other C1 metabolizing bacteria, in response to nitrate. This Example describes the identification of these nitrate inducible genes and their deduced promoter regions.

Specifically, Methylomonas sp. 16a was grown at 30° C. in BTZ-3 medium with either 10 mM ammonium chloride or 10 mM sodium nitrate as the nitrogen source. Cultures (typically 20 ml)at exponential phase ($OD_{660}$=0.3) were harvested for RNA isolation. Total RNA was isolated, labeled with fluorescent dyes, and used as probe on microarrays as described in Example 2. To identify genes specifically induced in the presence of nitrate, microarray hybridization experiments using probes made from RNA samples from these two growth conditions were compared. The ratio of spot intensities for each gene between nitrate and ammonia samples was used to identify two genes that were induced in the presence of nitrate (Table 4).

TABLE 4

Induction of Genes Involved In Nitrate Utilization In Methylomonas

| Gene | Description | Fold of Induction* |
| --- | --- | --- |
| nrtA | nitrogen transporter | 64 |
| glnB | nitrogen regulator protein | 26 |

*Units in fold induction (in the presence of nitrate) vs. control (in the presence of ammonia).

Table 5 is a description of the nitrate induced genes discovered from Methylomonas 16a. More specifically, Table 5 illustrates the relationship of the amino acid sequences encoded by these genes to known sequences in the art. All sequences were compared by conducting BLAST (Basic Local Alignment Search Tool; Altschul, S. F., et al., J. Mol. Biol. 215:403–410 (1993) searches for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL, and DDBJ databases). The nitrate induced gene DNA sequences were translated in all reading frames and compared for similarity to all publicly available protein sequences contained in the "nr" database using the BLASTX algorithm (Gish, W. and States, D. J. Nature Genetics 3:266–272 (1993)) provided by the NCBI. The results of the BLASTX comparison are given below in Table 5, which gives the known protein sequence to which the amino acid sequence encoded by each of the induced genes has the most identity and similarity. The Expect value estimates the statistical significance of the match, specifying the number of matches, with a given score, that are expected by chance in a search of a database of this size.

*Methylomonas* and other C1 metabolizing bacteria, in response to low pH. This Example describes the identification of the gene encoding glyoxalase 11 and its deduced promoter region.

Specifically, *Methylomonas* sp. 16a was grown at 30° C. in BTZ-3 medium without nitrate and with 5 mM ammo-

TABLE 5

Nitrate Induced Genes Identified From Methylomonas 16a

| Gene Name | Similarity Identified | SEQ ID NOs | % Identity[a] | % Similarity[b] | E-value[c] | Citation |
|---|---|---|---|---|---|---|
| nrtA | NITRATE TRANSPORT PROTEIN NRTA emb\|CAA68041.2\| (X99709) mutation of nrtA impairs active nitrate/nitrite transport [Anabaena sp. | 1, 2 | 34 | 49 | 9e–56 | Frias, J. E., et al., "Nitrate assimilation gene cluster from the heterocyst-forming cyanobacterium Anabaena sp. strain PCC 7120", J. Bacteriol. 179 (2): 477–486 (1997). |
| glnB | gb\|AAC46397.1\| (U91902) PII-protein [*Azotobacter vinelandii*] | 4, 5 | 76 | 89 | 2e–46 | Meletzus, D., et al., "Characterization of the glnK-amtB operon of *Azotobacter vinelandii*", J. Bacteriol. 180 (12): 3260–3264 (1998). |

[a]% Identity is defined as percentage of amino acids that are identical between the two proteins.
[b]% Similarity is defined as percentage of amino acids that are identical or conserved between the two proteins.
[c]Expect value. The Expect value estimates the statistical significance of the match, specifying the number of matches, with a given score, that are expected in a search of a database of this size absolutely by chance.

Following the identification of these nitrate induced genes, the genomic DNA sequence surrounding the coding region ATG start site for each gene was analyzed by PSI-BLAST (Altschul, S. F. et al., *Nucleic Acids Res.* 25:3389–340 (1997)) to identify other ORFs in the proximity. It was determined that there was no ORF in the same orientation located upstream of either coding region, indicating that each coding region was not iternal to an operon and therefore each gene included a promoter region. For the nrtA gene, the nucleotide region spanning from 408 bases upstream of the ATG start site (ATG at nucleotide=1 of SEQ ID NO:1) to 143 bases downstream of the ATG start site was selected as being sufficient to contain the promoter region. This region of DNA is provided as SEQ ID NO:3.

For the nitrogen regulating PII-protein (glnB) gene, the nucleotide region spanning from 444 bases upstream of the ATG start site (ATG at nucleotide=1 of SEQ ID NO:4) to 107 bases downstream of the ATG start site was selected as being sufficient to contain the promoter region. This region of DNA is provided as SEQ ID NO:6.

Example 4

Identification of a pH Induced DNA Region in *Methylomonas*

Using a *Methylomonas* DNA microarray prepared according to the methods described in Example 2, Applicants identified one pH inducible gene. The promoter of this gene can be employed for directing chimeric gene expression in nium chloride. The pH in the medium was adjusted with HCl to 5.5 when the cell density reached exponential phase ($OD_{660}$=0.3). After 45 min of treatment the culture was harvested, and total RNA was isolated labeled with fluorescent dyes, and used as probe on microarrays as described in Example 2. To identify genes induced by lowering the pH, microarray hybridization experiments using probes made from RNA samples prepared from treated (pH 5.5) and untreated (pH 7.0) cultures were compared. The ratio of spot intensities for each gene between treated and untreated samples was used to identify a gene that was induced in response to a change in pH (Table 6).

TABLE 6

Gene Induced in Response to pH Modification In Methylomonas

| Gene | Description | Fold of Induction* |
|---|---|---|
| glyoxII | putative glyoxalase II | 35 |

*Units in fold induction (pH 5.5) vs. control (pH 7.0).

Table 7 is a description of the pH induced gene discovered from *Methylomonas* 16a. More specifically, Table 7 illustrates the relationship of the aminio acid sequence encoded by this gene to known sequences in the art. The sequence was analyzed by conducting BLAST searches, as described in Example 3.

TABLE 7 pH Induced Genes Identified From Methylomonas 16a

| Gene Name | Similarity Identified | SEQ ID NOs | % Identity[a] | % Similarity[b] | E-value[c] | Citation |
|---|---|---|---|---|---|---|
| glyox II | >gb|AAB17995.1| (U74610) glyoxalase II [*Arabidopsis thaliana*] | 7, 8 | 51 | 68 | 4e-59 | ACCESSION H96575 Theologis, A., et al, Sequence and analysis of chromosome 1 of the plant *Arabidopsis thaliana* Nature 408 (6814), 816–820 (2000) |

[a]% Identity is defined as percentage of amino acids that are identical between the two proteins.
[b]% Similarity is defined as percentage of amino acids that are identical or conserved between the two proteins.
[c]Expect value. The Expect value estimates the statistical significance of the match, specifying the number of matches, with a given score, that are expected in a search of a database of this size absolutely by chance.

Following the identification of this pH induced gene, the genomic DNA sequence surrounding the coding region ATG start site was analyzed by PSI-BLAST (Altschul, S. F. et al., *Nucleic Acids Res.* 25:3389–340 (1997)) to identify other ORFs in the proximity. It was determined that there was no ORF in the same orientation located upstream of the this coding region, indicating that a promoter region was located upstream of this ORF. Thus, the nucleotide region spanning from −423 bases upstream of the ATG start site (ATG at nucleotide=1 of SEQ ID NO:7) to 156 bases downstream of the ATG start site was selected as being sufficient to contain the promoter region. This region of DNA is provided as SEQ ID NO:9.

Example 5

Identification of Temperature Induced DNA Region in *Methylomonas*

Using a *Methylomonas* DNA microarray prepared according to the methods described in Example 2, Applicants identified one temperature inducible gene. The promoter of this gene can be employed for directing chimeric gene expression in *Methylomonas* and other C1 metabolizing bacteria, when temperature is modified as an inducing condition. This Example describes the identification of htpg and its deduced promoter region.

Specifically, *Methylomonas* sp. 16a was grown at 30° C. in BTZ-3 medium with 5 mM ammonium chloride. The temperature of the culture was shifted to 42° C. when the cell density reached exponential phase ($OD_{660}$=0.3). After 45 min of treatment the culture was harvested and total RNA was isolated, labeled with fluorescent dyes, and used as a probe on microarrays as described in Example 2. To identify genes induced by increasing the temperature, microarray hybridization experiments using probes made from RNA samples from treated and untreated cultures were compared. The ratio of spot intensities for each gene between treated and untreated samples was used to identify those that were induced at higher temperature (Table 8).

TABLE 8

Gene Induced in Response to Temperature Modification In Methylomonas

| Gene | Description | Fold of Induction* |
|---|---|---|
| htpg | Heat shock protein | 16 |

*Units in fold induction (t = 42° C.) vs. control (t = 30° C.).

Table 9 is a description of the temperature induced gene discovered from *Methylomonas* 16a. More specifically, Table 9 illustrates the relationship of the amino acid sequence encoded by this gene to known protein sequences in the art. The sequence was analyzed by conducting BLASTX searches, as described in Example 3.

TABLE 9

Temperature Induced Genes identified From Methylomonas 16a

| Gene Name | Similarity Identified | SEQ ID NOs | % Identity[a] | % Similarity[b] | E-value[c] | Citation |
|---|---|---|---|---|---|---|
| htpg | >sp|P10413| HTPG_ECOLI heat shock protein HTPG (high temperature protein G) (heat | 10, 11 | 57 | 74 | 0.0 | Bardwell J. C. A., Craig E. A.; "Eukaryotic Mr 83,000 heat shock protein has a homologue in *Escherichia coli*", Proc. Nati. Acad. Sci. U.S.A. |

TABLE 9-continued

Temperature Induced Genes identified From Methylomonas 16a

| Gene Name | Similarity Identified | SEQ ID NOs | % Identity[a] | % Similarity[b] | E-value[c] | Citation |
|---|---|---|---|---|---|---|
| | shock protein C62.5) | | | | | 84: 5177–5181 (1987). |

[a]% Identity is defined as percentage of amino acids that are identical between the two proteins.
[b]% Similarity is defined as percentage of amino acids that are identical or conserved between the two proteins.
[c]Expect value. The Expect value estimates the statistical significance of the match, specifying the number of matches, with a given score, that are expected in a search of a database of this size absolutely by chance.

Following the identification of this temperature induced gene, the genomic DNA sequence surrounding the coding region ATG start site was analyzed by PSI-BLAST (Altschul, S. F. et al., *Nucleic Acids Res.* 25:3389–340 (1997)) to identify other ORFs in the proximity. It was determined that there was no ORF in the same orientation located upstream of the coding region, indicating that it was not internal to an operon and therefore the gene included a promoter region. The nucleotide region spanning from 540 bases upstream of the ATG start site (ATG at nucleotide=1 of SEQ ID NO:10) to 110 bases downstream of the ATG start site was selected as being sufficient to contain the promoter region. This region of DNA is provided as SEQ ID NO:12.

Example 6

Identification of Constitutively Expressed Genes when Methane and Methanol were Used as the Carbon Sources in *Methylomonas*

Using a *Methylomonas* DNA microarray prepared according to the methods described in Example 2, Applicants identified methane and methanol induced genes. The promoters of these genes can be employed for directing chimeric gene expression in *Methylomonas* and other C1 metabolizing bacteria, when cultures are grown in the presence of methane and/or methanol. This Example describes the identification of genes that are highly expressed when grown on methane and methanol and their deduced promoter regions.

Identification of these genes takes advantage of the capability of DNA microarray experiments to estimate gene expression levels. *Methylomonas* sp. 16a cultures were grown in BTZ-3 medium with 25% methane in air or 80 mM methanol. Cultures at exponential phase were harvested, RNA was isolated and each sample was labeled with Cy5 fluorescent dye. *Methylomonas* sp. 16a genomic DNA was labeled with Cy3 dye as described in Example 2. The genomic DNA probe was combined with each RNA-derived probe separately. The two mixed probe samples were hybridized to separate slides. After quantification, the ratio between the RNA (Cy5) and DNA probes (Cy3) was calculated for each spot on the two microarrays. The mRNA abundance for each gene was estimated based on the ratio of an individual gene divided by the sum of all ratios as described in Wei Y., et al. (*J. Bacteriol.* 183(2):545–56 (2001)). Subsequently, the expression level for each gene was ranked according to its mRNA abundance. Two genes with high levels of expression when grown on methane or methanol were identified (Table 10). The moxF gene involved in methanol metabolism was ranked #3 when grown on methane and was ranked #22 when grown on methanol. The hps gene was ranked #14 when grown on methane and was ranked #57 when grown on methanol.

TABLE 10

Ranking of highly expressed genes of Methylomonas when grown on methane or methanol

| Gene | Description | Methane | Methanol |
|---|---|---|---|
| moxF | Methanol dehydrogenase subunit | 3 | 22 |
| hps | Hexulose-6-phosphate synthase | 14 | 57 |

Table 11 is a more detailed description of these two genes discovered from *Methylomonas* 16a. More specifically, Table 11 illustrates the relationships of the amino acid sequences encoded by these genes to known protein sequences in the art. All sequences were analyzed by conducting BLASTX searches, as described in Example 3.

TABLE 11

Proteins Encoded by Highly Expressed Genes of Methylomonas when Grown on Methane or Methanol

| Gene Name | Similarity Identified | SEQ ID NOs | % Identity[a] | % Similarity[b] | E-value[c] | Citation |
|---|---|---|---|---|---|---|
| moxF | pir\|A47120 alcohol dehydrogenase (acceptor) (EC 1.1.99.8) large chain MoxF precursor - Methylomonas sp. | 13, 14 | 60 | 76 | 1e-12 | Waechter-Brulla, D., et al., "Methanol oxidation genes in the marine methanotroph Methylomonas sp. strain A4", J. Bacteriol. 175 (12): |

TABLE 11-continued

Proteins Encoded by Highly Expressed Genes of Methylomonas when Grown on Methane or Methanol

| Gene Name | Similarity Identified | SEQ ID NOs | % Identity[a] | % Similarity[b] | E-value[c] | Citation |
|---|---|---|---|---|---|---|
| | (fragment) gb\|AAA25302.1\| (L11308) methanol dehydrogenase [Methylomonas sp.] | | | | | 3767–3775 (1993). |
| hps | gb\|AAG29505.1\|AF 294615_1 (AF294615) 3-hexulose-6-phosphate synthase [Aminomonas aminovorus | 19, 20 | 55 | 64 | 3e-55 | GeneBank accession number: AAG29505 |

[a]% Identity is defined as percentage of amino acids that are identical between the two proteins.
[b]% Similarity is defined as percentage of amino acids that are identical or conserved between the two proteins.
[c]Expect value. The Expect value estimates the statistical significance of the match, specifying the number of matches, with a given score, that are expected in a search of a database of this size absolutely by chance.

Following the identification of these genes, the genomic DNA sequence surrounding the coding region ATG start site for each gene was analyzed by PSI-BLAST (Altschul, S. F. et al., Nucleic Acids Res. 25:3389–340 (1997)) to identify other ORFs in the proximity. It was determined that there was no ORF in the same orientation located upstream of each coding region, indicating that they were not internal to operons and therefore the genes included promoter regions. For the moxF gene, the nucleotide region spanning from 500 bases upstream of the ATG start site (ATG at nucleotide=1 of SEQ ID NO:13) to 196 bases downstream of the ATG start site was selected as being sufficient to contain the promoter region. This region of DNA is provided as SEQ ID NO:15.

For the hps gene, the nucleotide region spanning from 520 bases upstream of the ATG start site (ATG at nucleotide=1 of SEQ ID NO:16) to the ATG start site was selected as being sufficient to contain the promoter region. This region of DNA is provided as SEQ ID NO:18.

Example 7

Demonstration of Activity of moxF Promoter by Expressing a Marker Gene in Methylomonas To show the promoter activity of the selected promoter sequence for the moxF gene, the promoter was used to express the β-galactosidase (lacZ) reporter gene. The promoter fragment was amplified by standard PCR procedures from Methylomonas sp. 16a genomic DNA using the primer pair:

[SEQ ID NO:19]
5'-CAGGATCCGCGCCGTATGCTTTCGAATCCGCC-3'

[SEQ ID NO:20]
5'-CAGGATCCTGGAGAGCTGTTCCAGCTCCTTGTTC-3'

The amplified promoter fragment was digested with BamHI and ligated to BamHI digested pTJS75LacZKam. Plasmid pTJS75LacZKam is the pTJS75 vector (Schmidhauser and Helinski, v164 #1 p46–455 (1985)) to which a β-galactosidase (lacZ) coding region had been added (FIG. 1). Plasmid pTJS75 is a broad host range plasmid belonging to the IncP group. The resulting plasmid was transformed into Methylomonas sp. 16a and colonies containing the plasmid were grown on LB plates containing x-gal (5-bromo-3-indoyl-β-d-galactopyranoside). Visual inspection of the colonies revealed that some were blue in color, indicating that the x-gal substrate was converted by the β-galactosidase enzyme to the indigo derivative. Plasmid DNA from these colonies was analyzed by restriction enzyme digestion and showed that the moxF promoter fragment was oriented towards the lacZ coding region. Thus β-galactosidase enzyme was expressed, indicating that the moxF promoter region fragment had promoter activity in Methylomonas sp. 16a.

Example 8

Use of hps Promoter to Drive Foreign Gene Expression in Methylomonas sp. 16a and Escherichia coli Example 8 demonstrates that the hps promoter is useful to drive foreign gene expression in Methyolomonas sp. 16a and E. coli. This was tested by amplifying an hmps promoter fragment from genomic DNA, cloning the promoter into a plasmid containing the carotenoid gene cluster crtEXYIBZ such that expression of the crtZ gene was driven by the hps promoter, transforming this plasmid into E. coli, and then detecting the presence of zeaxanthin glucosides. Transformation of the plasmid into Methyolomonas 16a via bacterial conjugation also resulted in detection of zeaxanthin glucosides. As the crtZ gene, encoding β-carotene hydroxylase, catalyses the hydroxylation reaction from β-carotene to zeaxanthin, the detection of zeaxanthin glucosides confirmed the ability of the hps promoter to drive the chimeric gene expression of crtZ.

Amplification of the hps Promoter

A 500 bp DNA fragment (SEQ ID NO:18) containing the hps promoter was amplified from Methylomonas 16a genomic DNA using the following primers in a PCR:

```
5'-CCCATGGGTTCGGAATCCCTGA-3'                                    [SEQ ID NO:21]

[SEQ ID NO:22]
5'-GGAATTCCTCCTCTCCGAAAGTTTTTAATTATTAG-3'
```

The thermocycler conditions were set for 30 cycles at 94° C. for 30 sec, 61° C. for 30 sec and 72° C. for 2 min, followed by a final extension at 72° C. for 5 min. The 500 bp PCR product was purified using a Qiagen PCR purification kit, digested with NcoI and EcoRI for 1 hr at 37° C. and then purified following gel electrophoresis in 1% (w/v) agarose. The NcoI/EcoRI-digested PCR product was ligated to NcoI/EcoRI-digested pBHR1 (MoBiTec, LLC, Marco Island, Fla.) and the ligated DNA was used to transform *E. coli* DH5α. Transformants were selected on LB agar containing kanamycin (50 μg/ml). Analysis of the plasmid DNA from one transformant by restriction enzyme digestion and gel electrophoresis confirmed the presence of the expected plasmid, designated pHPS (FIG. 2A).

The crtEXYIBZ gene cluster from *Pantoea stweartii* was obtained on a 6255 bp EcoRI fragment from pCRT1 (WO 02/18617). In this gene cluster, the crtZ coding region is in opposite orientation to the other coding regions in the cluster and must be transcribed from a separate promoter. The 6255 bp EcoRI fragment containing the crt EXYIBZ coding regions was ligated to pHPS that had been digested with EcoRI and dephosphorylated with calf intestinal alkaline phosphatase (Gibco/BRL). The ligated DNA was used to transform *E. coli* DH5a. Transformants were selected on LB agar containing kanamycin (50 μg/ml). Analysis of restriction enzyme digested plasmid DNA from one transformant demonstrating yellow colony color confirmed the presence of a plasmid with the EcoRI fragment oriented such that the chloramphenicol acetyltransferase gene promoter (CAT promoter) is adjacent to the crtEXYIB coding regions, which was designated pCRT18 FIG. 2B). The yellow color indicated that carotenoids were being produced. In pCRT18 expression of the crtZ gene, encoding β-carotene hydroxylase, is directed from the *Methylomonas* 16a hps promoter (FIG. 2B). If the crtZ gene were expressed, then one would expect a transconjugant containing pCRT18 to synthesize zeaxanthin glucosides since these are derived from β-carotene by the β-carotene hydroxylase activity encoded by crtZ.

Cells of this colony were grown and assayed by HPLC as described in the general methods. The HPLC analysis showed peaks that eluted at 10.767–11.300, consistent with the expected profile for the mono- and diglucosides of zeaxanthin (eluting earlier than zeaxanthin, which has a rentention time of approximately 13.5 min). Thus zeaxanthin glucosides were observed in *E. coli* containing pCRT18, indicating that the *Methylomonas* 16a hps promoter directed heterologous gene expression in a bacterial host other than *Methylomonas*.

Plasmid pCRT18 was transferred into *Methylomonas* 16a by tri-parental conjugal mating. The *E. coli* helper strain containing pRK2013 and the *E. coli* DH5α donor strain containing pCRT18 were each grown overnight in LB medium containing kanamycin (50 μg/mL), washed three times in LB, and resuspended in a volume of LB representing approximately a 60-fold concentration of the original culture volume. The *Methylomonas* 16a recipient was grown for 48 hr in Nitrate liquid "BTZ-3" medium in an atmosphere containing 25% (v/v) methane, washed three times in BTZ-3, and resuspended in a volume of BTZ-3 representing a 150-fold concentration of the original culture volume. The donor, helper, and recipient cell pastes were combined on the surface of BTZ-3 agar plates containing 0.5% (w/v) yeast extract in ratios of 1:1:2, respectively. Plates were maintained at 30° C. in 25% methane for 16–72 hr to allow conjugation to occur, after which the cell pastes were collected and resuspended in BTZ-3. Dilutions were plated on BTZ-3 agar containing kanamycin (50 μg/mL) and incubated at 30° C. in 25% methane for up to 1 week. Transconjugants were streaked onto BTZ-3 agar with kanamycin (50 μg/mL) for isolation. Analysis of the plasmid DNA isolated from these transconjugants by restriction enzyme digestion confirmed the presence of pCRT18.

For analysis of carotenoid composition, transconjugants were cultured in 25 ml BTZ-3 containing kanamycin (50 μg/mL) and incubated at 30° C. in 25% methane as the sole carbon source for up to 1 week. The cells were harvested by centrifugation and frozen at −20° C. After thawing, the pellets were extracted and carotenoid content was analyzed by HPLC according to the methodology of the General Methods above. HPLC analysis of extracts from *Methylomonas* 16a containing pCRT18 confirmed the synthesis of zeaxanthin glucosides (FIG. 2C). Specifically, peaks eluted at 10.767–11.300, consistent with the expected profile for the mono- and diglucosides of zeaxanthin (eluting earlier than zeaxanthin, which has a rentention time of approximately 13.5 min).

Since plasmid pCRT1, containing the same crtEXYIBZ gene cluster as pCRT18 but lacking the *Methylomonas* 16a hps promoter, only conferred upon *Methylomonas* 16a the ability to produce α-carotene (WO 02/18617), the appearance of zeaxanthin glucosides in *Methylomonas* 16a containing pCRT18 confirmed that crtZ was expressed from the hps promoter.

To eliminate the formation of zeaxanthin glucosides, the crtX gene encoding zeaxanthin glucosyl-transferase was deleted from pCRT18. The 5149 bp EcoRV (position 1107)/EcoRI (position 6256) fragment of pCRT18 was replaced with a 3870 bp EcoRV (position 1107)/EcoRI (position 4977) fragment from which the crtX gene was deleted. Using PCR-mediated overlap extension, the crtX gene was deleted from the crtEXYIBZ gene cluster in three PCR steps. Template DNA for the first two reactions was a plasmid named pCRT2, which contains the complete crtEXYIBZ gene cluster without a promoter. First, the crtE coding region was amplified with the primers TRCcrtEF and CrtYER (SEQ ID NO:23, 24), incorporating 23 bases of crtY homology on the reverse primer.

```
                                                                [SEQ ID NO:23]
5'-CGGAATTCCCGCCCTGCCACTCATCGC-3'

[SEQ ID NO:24]
5'CCAGAATGAGATCATAGTGCGGTTGCATGCAGCATCCTTAA
CTGACGGCAG-3'
```

The 1373 bp PCR product was gel purified and used as template in the third polymerase chain reaction.

Second, the crtYIB coding regions were amplified together with primers CrtEYF and CrtBR (SEQ ID NO:25, 26), incorporating 26 bases of crtE homology on the forward primer.

```
                                                                [SEQ ID NO:25]
5'CTGCCGTCAGTTAAGGATGCTGCATGCAACCGCACTAT
```

-continued

GATCTCATTCTGG

[SEQ ID NO:26]
5'-GCGAATTCGCTAGCGGCTAGATCGGGCGCTGCC-3'

The 3604 bp PCR product was gel purified and used as template in the third polymerase chain reaction.

In the third PCR step, the products of the first two reactions were combined, primed to each other via their 23 bases of perfect homology, and amplified with the two outermost primers, TRCcrtEF and CrtBR (SEQ ID NO:23, 26). The resulting 4952 bp product contained the gene cluster crtEYIB, excluding the crtX gene entirely. A 3870 bp EcoR1/EcoRV digestion fragment which includes crtE, crtY, crtI, and a portion of crtB was ligated into EcoRV and EcoRI digested pCRT18, replacing the 5149 bp EcoRV/EcoR1 fragment. The resulting plasmid, pCRT24 (FIG. 3A), was transferred into *Methylomonas* 16a by tri-parental conjugal mating and the transconjugants were analyzed for their carotenoid composition by HPLC, as described in the General Methods.

Zeaxanthin (retention time 13.500 min) and cryptoxanthin (retention time 14.767 min) were produced in *Methylomonas* 16a containing pCRT24 (FIG. 3B) demonstrating the conversion of P-carotene (retention time 16.233 min) by the crtZ gene product, and thereby expression of the crtZ coding region from the hps promoter was confirmed.

What is claimed is:

1. An isolated nucleic acid molecule encoding a nitrate inducible gene selected from the group consisting of:
   (a) an isolated nucleic acid molecule encoding the amino acid sequence as set forth in SEQ ID NO:2;
   (b) an isolated nucleic acid molecule that hybridizes with (a) under stringent conditions using washes with 0.1× SSC, 0.1% SDS, 65°; or an isolated nucleic acid molecule that is complementary to (a), or (b), wherein said isolated nucleic acid molecule encodes a nitrate transport protein.

2. The isolated nucleic acid molecule of claim 1 as set forth in SEQ ID NO:1.

3. An isolated nucleic acid molecule comprising a first nucleotide sequence encoding a nrtA enzyme of at least 464 amino acids that has at least 90% identity based on the Smith-Waterman method of alignment when compared to a polypeptide having the sequence as set forth in SEQ ID NO:2;

or a second nuclectide sequence comprising the complement of the first nucleotide sequence.

* * * * *